(12) United States Patent
Ridgway et al.

(10) Patent No.: US 7,378,427 B2
(45) Date of Patent: May 27, 2008

(54) PROCESSES FOR PREPARING 6-ALKYL-5-ARYLSULFONYL-DIHYDROPHENANTHRIDINES

(75) Inventors: Brian Hugh Ridgway, Belmont, CA (US); William Jay Moore, Collegeville, PA (US); Mark Anthony Ashwell, Carlisle, MA (US); William Ronald Solvibile, East Windsor, NJ (US); Amy Tsai-Ting Lee, Los Altos, CA (US); Molly Elizabeth Hoke, Hightstown, NJ (US); Madelene Antane, West Windsor, NJ (US); Amedeo A. Failli, Princeton Junction, NJ (US)

(73) Assignee: Wyeth, Madison, NJ (US)

( * ) Notice: Subject to any disclaimer, the term of this patent is extended or adjusted under 35 U.S.C. 154(b) by 299 days.

(21) Appl. No.: 11/155,851

(22) Filed: Jun. 17, 2005

(65) Prior Publication Data

US 2006/0025436 A1    Feb. 2, 2006

Related U.S. Application Data

(60) Provisional application No. 60/580,849, filed on Jun. 18, 2004.

(51) Int. Cl.
*A61K 31/44* (2006.01)
*C07D 221/12* (2006.01)

(52) U.S. Cl. ...................... 514/298; 546/108
(58) Field of Classification Search ................ 546/108; 514/298
See application file for complete search history.

(56) References Cited

U.S. PATENT DOCUMENTS

| | | | |
|---|---|---|---|
| 5,326,875 A | 7/1994 | Talaga et al. ............... | 546/332 |
| 5,476,942 A | 12/1995 | Lassalle et al. ............. | 546/210 |
| 5,552,410 A | 9/1996 | Galtier et al. ............... | 514/311 |
| 5,703,244 A | 12/1997 | Li et al. ..................... | 548/557 |
| 5,786,496 A | 7/1998 | O'Halloran et al. ........ | 556/137 |
| 2003/0096019 A1 | 5/2003 | Currie et al. ............... | 424/649 |
| 2005/0113405 A1* | 5/2005 | Harnish et al. ............. | 514/298 |

FOREIGN PATENT DOCUMENTS

| | | |
|---|---|---|
| EP | 0 428 365 A1 | 5/1991 |
| EP | 0 496 393 B1 | 1/1995 |
| EP | 0 643 046 A1 | 3/1995 |
| EP | 0 643 047 A1 | 3/1995 |
| EP | 1 002 794 A1 | 5/2000 |
| FR | 2710067 A1 | 3/1995 |
| JP | 05170725 A2 | 7/1993 |
| JP | 08092082 A2 | 4/1996 |
| JP | 2564141 B2 | 12/1996 |
| JP | 2000026476 A2 | 1/2000 |
| JP | 2000038387 A2 | 2/2000 |
| KR | 9509521 B1 | 8/1995 |
| WO | 93/21149 A1 | 10/1993 |
| WO | 95/16682 A1 | 6/1995 |
| WO | 95/31438 A1 | 11/1995 |
| WO | 96/26223 A1 | 8/1996 |
| WO | 98/10761 A1 | 3/1998 |
| WO | 98/11108 A1 | 3/1998 |
| WO | 00/40561 A1 | 7/2000 |
| WO | 00/77010 A2 | 12/2000 |
| WO | 01/21602 A1 | 3/2001 |
| WO | 01/55085 A1 | 8/2001 |
| WO | 01/70228 A1 | 9/2001 |
| WO | 2004/050631 A1 | 6/2004 |
| WO | WO 2005 039581 A1 * | 5/2005 |
| WO | WO 2005 039582 A1 * | 5/2005 |
| WO | WO 2005 039583 A1 * | 5/2005 |

OTHER PUBLICATIONS

Ostendorf, M. et al, Eur. J. Org. Chem. 200, 105-113.*
Corey, E.J. et al, Journal of the American Chemical Society, 1987, 109, 7925-7926.*
Giannis, A. et al, Angew. Chem. Int. Ed. Engl, 1989, 28, 218-220.*
Adams, M. R. et al., "Inhibition of Coronary Artery Atherosclerosis by 17-beta Estradiol in Ovariectomized Monkeys," *Arterio.*, 1990, 10(6),1051-1057.
Alexander et. al., "Initiation of Hormone Replacement Therapy After Acute Myocardial Infarction Is Associated With More Cardiac Events During Follow-Up," *J. Am. Coll. Cardio.*, 2001, 38, 1-7.
Bauer M. A., Herrmann F., "Interleukin-6 in clinical medicine," *Ann. Hematol.*, 1991, 62, 203-210.
Cefalu, W., "The Use of Hormone Replacement Therapy in Postmenopausal Women with Type 2 Diabetes," *J Womens Health & Gender-based Med.*, 2001, 10(3), 241-255.
Cercek, B. et al., "Nuclear factor-κB Activity and arterial response to balloon injury," *Atherosclerosis* 131, 59-66 (1997).

(Continued)

*Primary Examiner*—Rita Desai
*Assistant Examiner*—John Mabry
(74) *Attorney, Agent, or Firm*—Pepper Hamilton LLP

(57) ABSTRACT

Synthetic methods are provided for production of compounds of the formula:

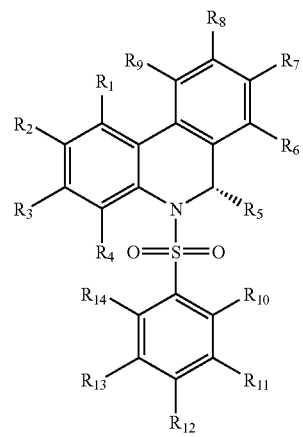

where $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ are as defined in the specification.

48 Claims, No Drawings

OTHER PUBLICATIONS

Chandrasekar, B. et al. "Ischemia-Reperfusion of Rat Myocardium Activates Nuclear Factor- κB and Induces Neutrophil Infiltration Via Lipopolysaccharide-Induced CXC Chemokine," *Circulation* 103, 2296-2302 (2001).

Lin, Chin-Chi et.al., "Pulmonary function changes and increased Th-2 cytokine expression and nuclear factor kB activation in the lung after sensitization and allergen challenge in brown Norway rats," *Immunol. Lett.*, 2000, 73, 57-64.

Delyani, J. A. et al., "Protection from Myocardial Reperfusion Injury by Acute Administration of 17 β-Estradiol," *J. Molec. Cell. Cardiol.*, 1996, 28, 1001-1008.

Dietrich, H. et al., "Mouse Model of Transplant Arteriosclerosis," *Arterioscler. Thromb. Vasc. Biol.* 20, 343-352 (2000).

Dubal et al., "Estradiol Modulates bcl-2 in Cerebral Ischemia: A Potential Role for Estrogen Receptors," *Journal of Neuroscience*, 1999, 19, 6385-6393.

Dubal et al., "Estrogen receptor α, not β, is a critical link in estradiol-mediated protection against brain injury," *Proceedings of the National Academy of Sciences of the United States of America*, 2001, 98(4), 1952-1957.

Felson, D. T. et al., "The effects of estrogen on osteoarthritis," *Curr Opinion Rheum*, 1998, 10, 269-272.

Grigg, R. et al., "Phenanthrene type heterocycles via Rh(I) catalysed [2+2+2]-cycloaddition and Pd(0) catalysed arylation" *Tetrahedron Lett*, 2000, 41(16), 3003-3006.

Grigg, R. et al., "Palladium Catalysed Intramolecular Coupling of Aryl and Benzylic Halides and Related Tandem Cyclisations. A Simple Synthesis of Hippadine", *Tetrahedron Lett*, 1991, 32(31), 3859-3862.

Grigg, R. et al., "Palladium Catalysed Triscyclisation-Anion Capture Queuing Cascades," *Tetrahedron Lett*, 1997, 38(10), 1825-1828.

Grodstein F. et. al., "Postmenopausal Hormone Use and Secondary Prevention of Coronary Events in the Nurses' Health Study," *Ann. Int. Med*, 2001, 135,1-8.

Grodstein, F. et. al., "A Prospective, Observational Study of Postmenopausal Hormone Therapy and Primary Prevention of Cardiovascular Disease," *Ann. Int. Med.*, 2000, 133, 933-41.

Heck, R.F., "Palladium-Catalyzed Reactions of Organic Halides with Olefins," *Acc Chem Res*, 1979, 12(4), 146-151.

Hulley, S. et. al., "Randomized Trial of Estrogen Plus Progestin for Secondary Prevention of Coronary Heart Disease in Postmenopausal Women," *J. Am. Med. Assoc.*, 1998, 280, 605-13.

Izumi, T. et al., "Blockade of the natriuretic peptide receptor guanylyl cyclase-A inhibits NF-κB activation and alleviation myocardial ischemia/reperfusion injury," *J. Clin. Invest*, 108, 203-213 (2001).

Kant, J., et al., "Reissert Compound Studies . XLV. The Phenanthridine Reissert Compound," *J Heterocycl Chem*, 1984, 21(2), 425-427.

Karas, R. H. et al., "Effects of Estrogen on the Vascular Injury Response in Estrogen Receptor α,β (Double) Knockout Mice," *Circ. Res.* 89, 534-539 (2001).

Kurebayashi S. et. al., "Characterization of Mechanisms of Interleukin-6 Gene Repression by Estrogen Receptor," *J. Steroid Biochem. Molec. Biol.*, 1997, 60, 11-17.

Lou, H. et al., "Inhibition of Transplant Coronary Arteriosclerosis in Rabbits by Chronic Estradiol Treatment Is Associated With Abolition of MHC Class II Antigen Expression," *Circulation* 94, 3355-3361 (1996).

Lundeen et al., "Rat uterine Complement C3 expression as a model for progesterone receptor modulators: characterization of a new progesterin trimegestone," *J Steroid Biochem Mol Biol*, 2001, 78, 137-143.

Mankin, et al., "Biochemical and Metabolic Abnormalities in Articular Cartilage from Osteo-Arthritic Human Hips," *Journal of Bone & Joint Surgery—American*, 1971, 53, 523-537.

Merchenthaler, et al., "The effect of estrogens and antiestrogens in a rat model for hot flush," *Maturitas*,1998, 30, 307-316.

Miura, M. et al., "Oxidative Cross-Coupling of N-(2'-Phenylphenyl) benzenesulfonamides of Benzoic and Naphthoic Acids with Alkenes Using a Palladium-Copper Catalyst System under Air," *J Org Chem*, 1998, 63(15), 5211-5215.

Nathan, L. et. al., "Estradiol Inhibits Leukocyte Adhesion and Transendothelial Migration in Rabbits In Vivo," *Circ. Res.*, 1999, 85, 377-385.

Patra, P.K. et al., "A New Regiospecific Method for the Synthesis of Substituted Phenanthridines and Benzo[j]phenanthridines via Aromatic ]- Annelation of 1-N-Benzenesulfonyl-3-[Bis(methylthio)methylene 1,2,3,4-tetrahydroquinoline-4-one," *Tetrahedron*, 1998, 54(34), 10167-10178.

Pelletier et al., "Osteoarthritis, an Inflammatory Disease," *Arthr. & Rheum.*, 2001, 44, 1237-1247.

Poole and Coombs, "Rheumatoid-Like Joint Lesions in Rabbits Injected Intravenously with Bovine Serum," *International Archives of Allergy & Applied Immunology*, 1977, 54, 97-113.

Reis et. al., "Estrogen Is Associated With Improved Survival in Aging Women With Congestive Heart Failure: Analysis of the Vesnarinone Studies," *J. Am. Coll. Cardio.*, 2000, 36, 529-33.

Shugrue et al., "Regulation of Progesterone Receptor Messenger Ribonucleic Acid in the Rat Medial Preoptic Nucleus by Estrogenic and Antiestrogenic Compounds: An in Situ Hybridization Study," *Endocrinology*, 1997, 138, 5476-5484.

Smirnoff, P. et al., "The Protective Effect of Estrogen Against Chemically Induced Murine Colon Carcinogenesis Is Associated With Decreased CpG Island Methylation and Increased mRNA and Protein Expression of the Colonic Vitamin D Receptor," *Oncology Research*, 1999, 11, 255-264.

Stetson, S. J. et al., "Cardiac Hypertrophy After Transplantation Is Associated With Persistent Expression of Tumor Necrosis Factor-α," *Circulation*, 2001, 104, 676-681.

Sullivan, T. R. et al. "Estrogen Inhibits the Response-to-Injury in a Mouse Carotid Artery Model," *J. Clin. Invst.*, 1995, 96, 2482-8.

Wallen, W. J. et al., "Gender-Differences in Myocardial Adaptation to Afterload in Normotensive and Hypertensive Rats," *Hypertension* 36, 774-779 (2000).

Yagi, K., "Short Communications—A Simple Fluorometric Assay for Lipoperoxide in Blood Plasma," *Biochemical Medicine*, 1976, 15, 212-216.

Yokoseki, O. et al., "*cis* Element Decoy Against Nuclear Factor- κB Attenuates Development of Experimental Autoimmune Myocarditis in Rats," *Circ. Res.* 89, 1-9 (2001).

Yuan et al., "Reversal of Obesity- and Diet-Induced Insulin Resistance with Salicylates or Targeted Disruption of *Ikkβ,*" *Science*, 2001, 293, 1673-1677.

Giannis, A. et al., "LiBH$_4$(NaBH$_4$)/Me$_3$SiCl, An Unusually Strong and Versatile Reducing Agent," *Angew. Chem. Int. Ed. Engl.*, 1989 28, 218.

Abramovitch, R.A. et al., "Intramolecular Cyclization of 2-Biarylsulfonyl Azides," *J Org Chem*, 1977, 42(17), 2914-2919.

Arnett, E.M. et al., "Weak Bases in Strong Acids. III. Heats of Ionization of Amines in Fluorosulfuric and Sulfuric Acids. A New General Basicity Scale," *J Amer Chem Soc*, 1970, 92(5), 1260-1266.

Barlos, K. et al., "Redox-Alkylierung von Tyrosin-Derviaten," *Liebigs Ann Chem*, 1986, (8), 1407-1412.

Bernotas, R.C. et al., "The Use of Triphenylphosphine/Diethyl Azodicarboxylate (DEAD) For the Cyclization of 1,4- and 1,5-Amino Alcohols," *Tetrahedron Lett*, 1991, 32(2), 161-164.

Burns, B. et al., "Palladium Catalysed Tandem Cyclisation-Anion Capture Processes. Part I. Background and Hydride Ion Capture by Alkyl- and π-Allyl-Palladium Species," *Tetrahedron*, 1992, 48(35), 7297-7320.

Casaschi, A. et al., "Palladium Catalyzed Tandem Cyclisation-Anion Capture. Part 5: Cascade Hydrostannylation-bis-cyclisation-intramolecular Anion Capture. Synthesis of Bridged- and Spiro-Cyclic Small and Macrocyclic Heterocycles," *Tetrahedron*, 2000, 56(38), 7541-7551.

Cho, H-S. et al., "Preparation and Scope of a Remarkably Robust Primary Alcohol Protective Group," *J Am Chem Soc*, 1994, 116(18), 8354-8355.

Davis, A.P. et al., "Mitsunobu Reactions with Methaneesulfonic Acid; The Replacement of Equatorial Hydroxyl Groups by Azide with Net Retention of Configuration," *Tetrahedron Lett*, 1997, 38(24), 4305-4308.

Fielding, M.R. et al., "Novel synthesis of oxindoles from carbamoyl chlorides via palladium catalysed cyclisation-anion capture," *Chem Commun*, 2000, (22), 2239-2240.

Giroux, A. et al., "One Pot Biaryl Synthesis via in situ Boronate Formation," *Tetrahedron Lett*, 1997, 38(22), 3841-3844.

Gomez-Vidal, J.A. et al., "Short, Highly Efficient Syntheses of Protected 3-Azido- and 4-Azidoproline and Their Precursors," *Org Lett*, 2001, 3(16), 2481-2484.

Harayama T. et al., "Synthesis of trisphaeridine and norchelerythrine through palladium-catalyzed aryl-aryl coupling reactions," *J Chem Soc, Perkin Trans. 1*, 2001, (5), 523-528.

Hassan, J. et al., "Synthesis of unsymmetrical biaryls via palladium-catalyzed coupling reaction of aryl halides," *Tetrahedron Lett*, 2000, 41, 8791-8794.

Hellwinkel, D. et al., "Möglichkeiten und Grenzen der anionisch induzierten Sulfonamid-Aminosulfon-Umlagerung," *Chem Ber*, 1985, 118(1), 66-85.

Humber, L.G. et al., "Etodolac, a Novel Antiinflammatory Agent. The Syntheses and Biological Evaluation of Its Metabolites," *J Med Chem*, 1988, 31(9), 1712-1719.

Larock, R.C. et al., "Synthesis of Indoles via Palladium-Catalyzed Heteroannulation of Internal Alkynes," *J Am Chem Soc*, 1991, 113(17), 6689-6690.

Buston, J.E.H. et al., "Meisenheimer rearrangements of N-allyl 2-azabornane derivatives," *J Chem Soc Perkin Trans 1*, 1999, (16), 2327-2334.

Nilsson, K. et al., "Regioselective Palladium-Catalyzed Tandem α-Arylation/Isomerization of Cyclic Enamides," *J Org Chem*, 1990, 55(8), 2464-2470.

Desmaële, D. et al., "Stereocontrolled Elaboration of Quarternary Carbon Centers through the Asymmetric Michael Reaction Using Chiral Imines: Enantioselective Synthesis of (+)-Aspidospermidine," *J Org Chem*, 1994, 59(9), 2292-2303.

Larock, R.C. et al., "Synthesis of 2,3-Disubstituted Indoles via Palladium-Catalyzed Annulation of Internal Alkynes," *J Org Chem*, 1998, 63(22), 7652-7662.

Yamada, K. et al., "Asymmetric Reduction of Cyclic Imines with Chiral Sodium Acyloxyborohydrides," *J. Chem. Soc. Perkin Trans.* I, 265 (1983).

Gossler, H. et al., "Synthese und Eigenschaften von Biindolen," *Justus Liebigs Ann Chem*, 1977, (11-12), 1953-1958.

Kadow, J.F. et al., "Synthesis of Etoposide Lactam via a Mitsunobu Reaction Sequence," *Tetrahedron Lett*, 1989, 30(25), 3299-3302.

Karagiannis, K. et al., "Synthesis of cis-4-Hydroxy-L-proline and its Incorporation into Biologically Important Peptides," *Epitheor Klin Farmakol Farmakokinet Int'l. Ed.*, 1995, 9(2 and 3), 103-106.

Khilevich, A. et al., "A Versatile Approach For Synthesis of 2,3-Dimethyl Chroman-4-ones, Intermediate For Calanolide Anti-HIV Agents, Via Aldol/Mitsunobu Reactions," *Synth Commun*, 1996, 26(20), 3757-3771.

Larksarp, C, et al., "Palladium-Catalyzed Cyclocarbonylation of o-Iodoanilines with Heterocumulenes: Regioselective Preparation of 4(3H)-Quinazolinone Derivatives," *J Org Chem*, 2000, 65(9), 2773-2777.

Lee, B.H. et al., "Constituents of Microbial Iron Chelators. Alternate Syntheses of δ-N-Hydroxy-L-ornithine Derivatives and Applications to the Synthesis of Rhodotorulic Acid," *J Org Chem*, 1984, 49(13), 2418-2423.

Liu, L. et al., "Electrophilic Sulfur Transfer Reactions in Organic Synthesis. Preparation of a Diastereomer of the Key Macrocyclic Component of Griseoviridin," *J Org Chem*, 1986, 51(26), 5332-5337.

Macor, J.E. et al., "The use of o-Nitroarylacetonitriles in the Mitsunobu Reaction: Mechanistic Implications and Synthetic Applications," *Heterocycles*, 1993, 35(1), 349-365.

Macor, J.E. et al., "The Synthesis of a Conformationally Restricted Analog of the Anti-Migraine Drug Sumatriptan," *Tetrahedron Lett*, 1992, 33(52), 8011-8014.

Montero, J.L. et al., "Aminoacylation of Nucleosides. Mitsunobu Conditions versus Chemoenzymatic Route," *Tetrahedron Lett*, 1991, 32(39), 5357-5358.

Murata, M. et al., "Palladium-Catalyzed Borylation of Aryl Halides of Triflates with Dialkyloxyborane: A Novel and Facile Synthetic Route to Arylboronates," *J Org Chem*, 2000, 65, 164-168.

Nakajima, K. et al., "Synthetic Studies of Glutathione and Some Cyctine Peptides Via Aziridine Ring-Opening Reaction by $H_2S$," *Pept Chem*, 1983, vol. Date 1982, 20th, 19-24.

Ohtsuka, Y. et al., "Studies on Taxane Synthesis. II. Syntheses of 3,8,11,11-Tetramethyl-4-oxo- and 4,8,11,11-Tetramethyl-3-oxo-bicyclo[5.3.1]undec-8-enes Corresponding to the A- and B-Rings of Taxane Diterpenes," *Chem Pharm Bull*, 1988, 36(12), 4722-4736.

Suginome, M. et al., "New Access to 2,3-Disubstituted Quniolines through Cyclization of o-Alkylnylisocyanobenzenes," *Org Lett*, 1999, 1(12), 1977-1979.

Pansare, S.V. et al., "Synthesis of N-tert-Butoxycarbonyl-L-Serine β-Lactone and the p-Toluenesulfonic Acid Salt of (S)-3-Amino-2-Oxetanone," *Org Synth*, 1992, 70, 10-17.

Papaioannou, D. et al., "N-tritylated Derivatives of cis-4-Hydroxy-L-Proline and their Application in Peptide Synthesis," *Pept Proc Eur Pept Symp, 20th*, 1989; Meeting Date 1988, 91-3. Editor(s): Jung, Guenther; Bayer, Ernst. De Gruyter: Berlin, Fed. Rep. Ger.

Peaston, W.C. et al., "Azabenzocycloheptenones. Part VIII. Further Observations in the Dibenz[b,d]azepin-7-one Field," *J Chem Soc*, 1968, 19, 2481-2484.

Pungente, M.D. et al., "Synthesis and Stereochemical Elucidation of a 14-Membered Ring Phosphonate," *Org Lett*, 2001, 3(5), 643-646.

Russell, C. et al., "Palladium-Catalyzed Acylation of Unsaturated Halides by Anions of Enol Ethers," *J Am Chem Soc*, 1983, 105(4), 943-949.

S. Atarashi et al., "Asymmetric Reduction of 7,8-Difluoro-3-methyl-2H-1,4-benzoxazine. Synthesis of a Key Intermediate of (S)-(-)-Ofloxacin (DR-3355)," *J. Heterocyclic Chem.*, 1991 28, 329.

Shapiro, B.L. et al., "NMR Spectral Data: A Compilation of Aromatic Proton Chemical Shifts in Mono- and Di-substituted Benzenes," *J Phys Chem Ref Data*, 1977, 6(3), 919-991.

Shin, C-G. et al., "Practical Synthesis of Oxazoles Incorporated in α-Dehydroamino Acid and Dehydropeptide Structures," *Chem Lett*, 1993, (8), 1405-1408.

Skarzewski, J. et al., "Synthesis of $C_2$ symmetric primary vicinal diamines. Double stereospecific Mitsunobu reaction on the heterocyclic diols derived from tartaric acid," *Tetrahedron: Asymmetry*, 1997, 8(11), 1861-1867.

Takagi, K. et al., "Palladium(0)-catalyzed Synthesis of 2-Alkylbenzothiazoles by a Novel Thiation of 1-Amino-2-iodoarenes with Thiomides," *Chem Lett*, 1987, (5), 839-840.

Larock, R.C. et al., "Improved Procedures for the Palladium-Catalyzed Intermolecular Arylation of Cyclic Alkenes," *Tetrahedron Lett*, 1989, 30(20), 2603-2606.

Jeschke, T. et al., "A Novel Approach to Bz-Substituted Tryptophans via Pd-catalysed Coupling / Annulation," *Tetrahedron Lett*, 1993, 34(40), 6471-6474.

Larock, R.C. et al., "Palladium-catalyzed Annulation of Vinylic Cyclopropanes and Cyclobutanes," *Tetrahedron*, 1996, 52(8), 2743-2758.

Mori, M. et al., "Total Syntheses of Prothracarcin and Tomaymycin by Use of Palladium Catalyzed Carbonylation," *Tetrahedron*, 1986, 42(14), 3793-3806.

Torii, S. et al., "Syntheses of Chromones and Quinolones via Pd-Catalyzed Carbonylation of o-Iodophenols and Anilines in the Presence of Acetylenes," *Tetrahedron*, 1993, 49(31), 6773-6784.

Kadokami, T. et al., "Anti-Tumor Necrosis Factor-α Antibody Limits Heart Failure in a Transgenic Model," *Circulation*, 2001, 104, 1094-1097.

Ulmer, L. et al., "Mono- and Bisfunctionalization of Fullerenes With N-Containing Reactants," *J Inf Rec*, 1998, 24(3-4), 243-247.

Varasi, M. et al., "A Revised Mechanism for the Mitsunobu Reaction," *J Org Chem*, 1987, 52(19), 4235-4238.

Vicente, J. et al., "Synthesis and Reactivity of 2-Aminophenylpalladium(II) Complexes: Insertion Reactions of Oxygen and Carbon Monoxide into Carbon—Palladium Bonds—New Examples of 'Transphobia'," *Chem.—Eur J.*, 1999, 5(10), 3066-3075.

Walker, M.A., "An Unusual Tandem Cyclization-Stevens Rearrangement by Ph3P/DEAD or Bu3P/ADDP," *Tetrahedron Lett*, 1996, 37(45), 8133-8136.

Xiao, W-J. et al., Regioselective Carbonylative Heteroannulation of *o*-Iodothiophenols with Allenes and Carbon Monixide Catalyzed by a Palladium Complex: A Novel and Efficient Access to Thiochroman-4-one Derivatives, *J Org Chem*, 1999, 64(26), 9646-9652.

Yamada, K. et al., "Studies on 1,2,3,4-Tetrahydroisoquinolines. VI. Reutilization of the Unwanted (*R*)-Isomer of (*S*)-(—)-5,7-Dihydroxy-1-(3,4,5-trimethoxybenzyl)-1,2,3,4-tetrahydroisoquinoline (TA-073)," *Chem. Pharm. Bull.*, 31, 70 (1983).

Yen, Y-P. et al., "New Simple Synthesis of the Housefly Sex Attractant," *Org Prep Proced. Int.*, 1997, 29(4), 494-496.

Ziegler, C.B., et al., "Palladium-Catalyzed Vinylic Substitution with Highly Activated Aryl Halides," *J Org Chem*, 1978, 43(15), 2941-2946.

* cited by examiner

PROCESSES FOR PREPARING 6-ALKYL-5-ARYLSULFONYL-DIHYDROPHENANTHRIDINES

CROSS-REFERENCE TO RELATED APPLICATIONS

The present application claims benefit to U.S. Provisional Application Ser. No. 60/580,849, filed Jun. 18, 2004, which is incorporated herein by reference in its entirety.

FIELD OF THE INVENTION

This invention relates, in part, to arylsulfonyl-dihydrophenanthridines such as 6-alkyl-5-arylsulfonyl-dihydrophenanthridines and processes for their enantioselective preparation.

BACKGROUND OF THE INVENTION

6-Alkyl-5-arylsulfonyl-dihydrophenanthridine compounds are believed to be useful as ligands for the estrogen receptor (ER) devoid of the unwanted proliferative side effects associated with estrogen. Alternative synthetic methods for these and structurally related compounds are desired.

SUMMARY OF THE INVENTION

The present invention relates to compounds that are able to serve as ligands for the estrogen receptor but exhibit a more beneficial profile than that of classical estrogens. In some embodiments, the invention is directed to compounds of formula (I):

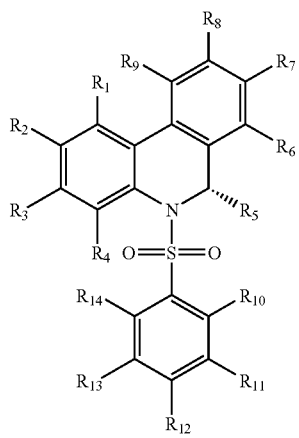

(I)

wherein $R_1$, $R_2$, $R_3$, $R_4$, $R_6$, $R_7$, $R_8$, $R_9$, $R_{10}$, $R_{13}$ and $R_{14}$ are independently, hydrogen, alkyl, halogen, or aryl;

$R_5$ is $C_1$-$C_{12}$ alkyl or $C_6$-$C_{20}$ aryl;

$R_{11}$ and $R_{12}$ are, independently, hydrogen, $C_1$-$C_{12}$ alkyl, or $OP_1$ where $P_1$ is hydrogen or a phenol protecting group, sulfamate or alkylcarbonate; or a pharmaceutically acceptable salt thereof, or a prodrug thereof. In certain preferred embodiments, one of $R_{11}$ and $R_{12}$ is $OP_1$ and the other is H. In certain of these embodiments, $R_{12}$ is $OP_1$.

In some aspects, the invention concerns methods of synthesizing a compound of formula I. One preferred method comprises: (a) providing a chiral, non-racemic compound of general formula (II)

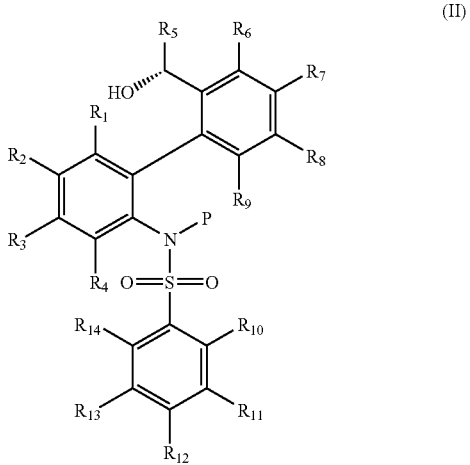

(II)

where P is hydrogen or an amino protecting group; (b) removing the optional amino protecting group P to produce an unprotected compound ; and (c) cyclizing the chiral, unprotected compound under Mitsunobu conditions such as in the presence of an alkyl- or arylphosphine and a diaryl- or dialkylazodicarboxylate in an aprotic solvent.

The chiral compounds having formula II are preferably obtained by reduction of the compounds having formula (III)

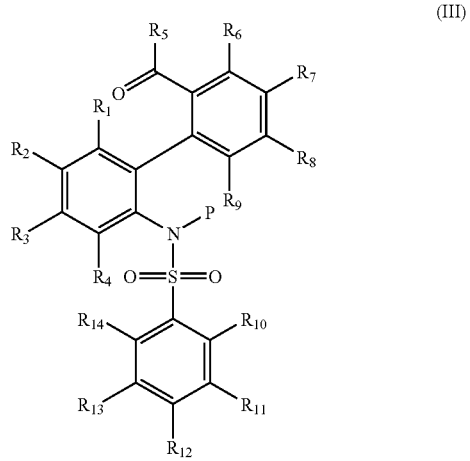

(III)

with a chiral reducing agent and a borane methyl sulfide complex.

Another preferred aspect of this invention concerns methods of synthesizing compounds of formula I by contacting a compound of formula (IV)

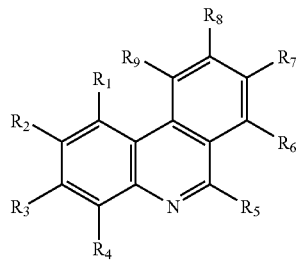
(IV)

with an arylsulfonyl chloride of formula (V)

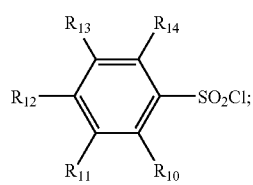
(V)

in the presence of a chiral reducing agent and a borane methyl sulfide complex.

In yet other preferred aspects, the invention concerns methods of synthesizing compounds of formula I by contacting a compound of formula (VI)

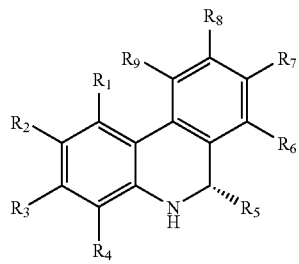
(VI)

with an arylsulfonyl chloride of formula (V)

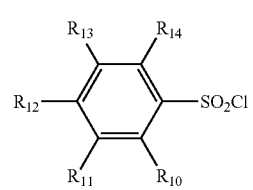
(V)

The chiral compounds having formula (VI)

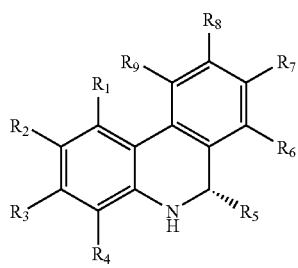
(VI)

are preferably obtained by reduction of the compounds having formula (IV)

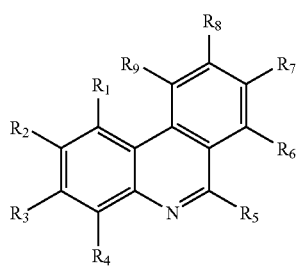
(IV)

with a chiral sodium triacyloxyborohydride reducing agent.

In other preferred embodiments, chiral compounds having formula (VI)

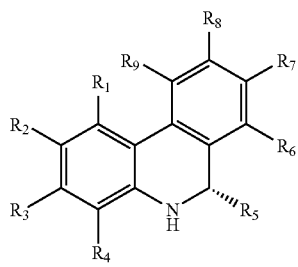
(VI)

are obtained by reduction of the compounds having formula (IV)

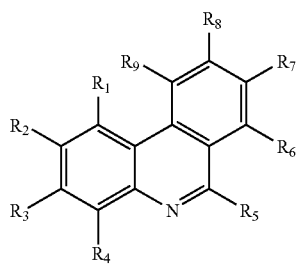
(IV)

with a chiral reducing agent in the presence of a metal borohydride and a halotrialkylsilane.

In other aspects the invention concerns compounds of formula I which are made by the processes described herein.

DETAILED DESCRIPTION

In a preferred process, compound I can be prepared from chiral, non-racemic compounds of the formula II by removing the optional amino protecting group and cyclizing the deprotected compound in the presence of an alkyl- or arylphosphine and a diaryl- or dialkylazodicarboxylate. This latter step is preferably performed in an aprotic solvent. In some aspects, the cyclization step is performed in tetrahydrofuran at a temperature from ambient to 70° C.

In some aspects, the alkyl- or arylphosphine is triphenylphosphine. In still other aspects the diaryl- or dialkylazodicarboxylate is diethyl- or di-tert-butylazodicarboxylate.

Certain methods concern compounds where $R_1$, $R_2$, $R_3$, $R_4$, $R_6$, $R_8$, $R_9$, $R_{10}$, $R_{11}$, $R_{12}$, $R_{13}$ and $R_{14}$ are each hydrogen. In other methods, $R_{11}$ and $R_{12}$ are independently, OH, or $R_{11}$ and $R_{12}$ are independently, $OP_1$, where $P_1$ is a phenol protecting group. In other methods, $R_{11}$ and $R_{12}$ are independently, hydrogen, $C_1$-$C_{12}$ alkyl, sulfamate or alkylcarbonate. In yet other methods, $R_7$ is $C_1$-$C_{12}$ alkyl, $C_6$-$C_{20}$ aryl, or halogen; and $R_5$ is $C_1$-$C_{12}$ alkyl or $C_6$-$C_{20}$ aryl. In certain preferred compositions $R_5$ is methyl, and $R_7$ is fluoro.

In some embodiments, the compound of formula (II) is obtained by reduction of the compound of formula (III)

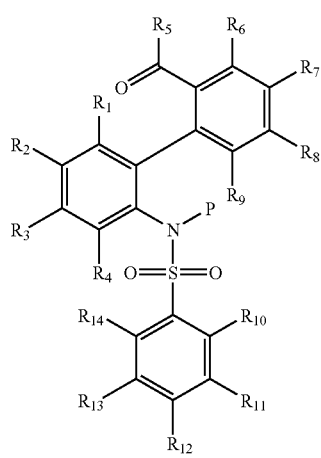

(III)

with a chiral reducing agent and a borane methyl sulfide complex. In certain embodiments, the chiral reducing agent is (S)-tetrahydro-1-methyl-3,3-diphenyl-1H,3H-pyrrolo[1,2-c][1,3,2]oxazaborole or [(+)-B-chlorodiisopinocampheylborane].

In yet another aspect, the invention concerns synthesizing a compound of formula I by (a) contacting a compound of formula (IV)

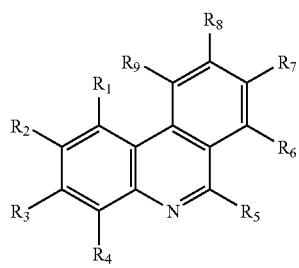

(IV)

with an arylsulfonyl chloride of formula (V)

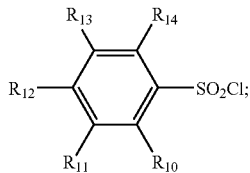

(V)

and (b) adding the mixture from step (a) to a chiral reducing agent and a borane methyl sulfide complex.

In some aspects, step (a) is performed in an aprotic solvent such as dichloromethane or toluene. In other aspects, the chiral reducing agent is (R)-tetrahydro-1-methyl-3,3-diphenyl-1H,3H-pyrrolo[1,2-c][1,3,2]oxazaborole.

In certain embodiments, $R_1$, $R_2$, $R_3$, $R_4$, $R_6$, $R_8$, $R_9$, $R_{10}$, $R_{11}$, $R_{12}$, $R_{13}$ and $R_{14}$ are each hydrogen. In some embodiments, one of $R_{11}$ and $R_{12}$ is OH. In other embodiments, one of $R_{11}$ and $R_{12}$ is $OP_1$. In other embodiments $R_{11}$ and $R_{12}$ are independently, hydrogen, $C_1$-$C_{12}$ alkyl, sulfamate or alkylcarbonate. In yet other embodiments, $R_7$ is $C_1$-$C_{12}$ alkyl, $C_6$-$C_{20}$ aryl, or halogen. In certain compositions, $R_7$ is fluoro. In some compositions $R_5$ is $C_1$-$C_{12}$ alkyl. In certain preferred compositions, $R_5$ is methyl.

Compound I can also be produced by contacting a compound of formula (VI)

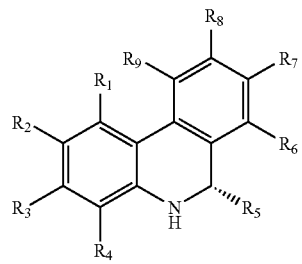

(VI)

with an arylsulfonyl chloride of formula (V)

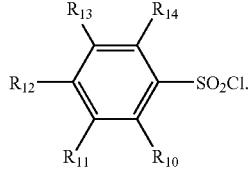

(V)

In some aspects, the reaction is performed in an aprotic solvent such as dichloromethane or toluene.

In certain embodiments, $R_1$, $R_2$, $R_3$, $R_4$, $R_6$, $R_8$, $R_9$, $R_{10}$, $R_{11}$, $R_{12}$, $R_{13}$ and $R_{14}$ are each hydrogen. In some embodiments, $R_{11}$ and $R_{12}$ are independently, OH. In other embodiments, $R_{11}$ and $R_{12}$ are independently, $OP_1$. In other embodiments $R_{11}$ and $R_{12}$ are independently, $C_1$-$C_{12}$ alkyl, sulfamate or alkylcarbonate. In yet other embodiments, $R_7$ is $C_1$-$C_{12}$ alkyl, $C_6$-$C_{20}$ aryl, or fluoro. In some compositions $R_5$ is alkyl. In certain preferred compositions, $R_5$ is methyl.

The chiral compounds having formula (VI)

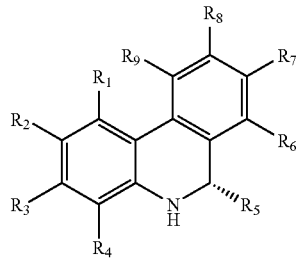

(VI)

are preferably obtained by reduction of the compounds having formula (IV)

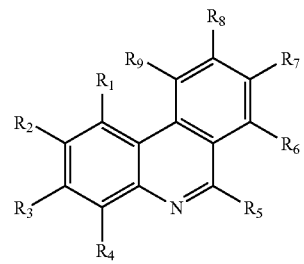

(IV)

with a chiral sodium triacyloxyborohydride reducing agent.

In some aspects, the reduction is performed in an aprotic solvent such as dichloromethane or toluene. In other aspects the chiral reducing agent is sodium (S)-hydrotris[1-(2-methylpropyl) 1,2-pyrrolidinedicarbozylato-$O^2$ ]borate(1-).

In certain embodiments, $R_1$, $R_2$, $R_3$, $R_4$, $R_6$, $R_8$, $R_9$, $R_{10}$, $R_{11}$, $R_{12}$, $R_{13}$ and $R_{14}$ are each hydrogen. In some embodiments, $R_{11}$ and $R_{12}$ are independently, OH. In other embodiments, $R_{11}$ and $R_{12}$ are independently, $OP_1$. In other embodiments $R_{11}$ and $R_{12}$ are independently, hydrogen, $C_1$-$C_{12}$ alkyl, sulfamate or alkylcarbonate. In yet other embodiments, $R_7$ is $C_1$-$C_{12}$ alkyl, $C_6$-$C_{20}$ aryl, or fluoro. In some compositions $R_5$ is $C_1$-$C_{12}$ alkyl. In certain preferred compositions, $R_5$ is methyl.

In other preferred embodiments, chiral compounds having formula (VI)

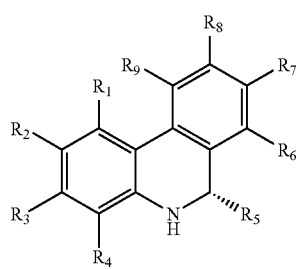

(VI)

are obtained by reduction of the compounds having formula (IV)

with a chiral reducing agent in the presence of a metal borohydride and a halotrialkylsilane.

In some aspects, the reduction is performed in an aprotic solvent such as tetrahydrofuran or toluene. In other aspects the chiral reducing agent is (R)-2-methyl-CBS-oxazaborolidine, the metal borohydride is lithium borohydride and the halotrialkylsilane is chlorotrimethylsilane.

In certain embodiments, $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ are each hydrogen. In some embodiments, $R_{11}$ and $R_{12}$ are independently, OH. In other embodiments, $R_{11}$ and $R_{12}$ are independently, $OP_1$. In other embodiments $R_{11}$ and $R_{12}$ are independently, hydrogen, $C_1$-$C_{12}$ alkyl, sulfamate or alkylcarbonate. In yet other embodiments, $R_7$ is $C_1$-$C_{12}$ alkyl, $C_6$-$C_{20}$ aryl, or fluoro. In some compositions $R_5$ is $C_1$-$C_{12}$ alkyl. In certain preferred compositions, $R_5$ is methyl.

The term "protecting group" is well understood by one skilled in the art. In particular one skilled in the art is aware of various protecting groups for use as amine, nitrogen, phenol, or oxygen protecting groups. As used herein, any of these groups that are compatible with the particular chemistry discussed herein may be used. Protecting groups, including phenol protecting groups, are described, for example, in T. W. Greene and P. G. M. Wuts, "Protecting Groups in Organic Synthesis" (1991). Particular examples of phenol protecting groups include methyl, benzyl, benzyloxymethyl, or allyl. Examples of amino protecting groups include methoxyethyl(trimethylsilyl) or methoxyethoxymethyl which can be readily removed by tetrabutylammonium fluoride or similar agent in a solvent such as tetrahydrofuran.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable aids when a compound of this invention contains a basic moiety. Salts may also be formed from organic and inorganic bases, such as alkali metal salts (for example, sodium, lithium, or potassium), alkaline earth metal salts, ammonium salts, alkylammonium salts containing 1-6 carbon atoms or dialkylammonium salts containing 1-6 carbon atoms in each alkyl group, and trialkylammonium salts containing 1-6 carbon atoms in each alkyl group, when a compound of this invention contains an acidic moiety.

The term "alkyl", as used herein, whether used alone or as part of another group, refers to a substituted or unsubstituted aliphatic hydrocarbon chain and includes, but is not limited to, straight and branched chains containing from 1 to 12 carbon atoms, preferably 1 to 6 carbon atoms, unless explicitly specified otherwise. For example, methyl, ethyl, propyl, isopropyl, butyl, i-butyl and t-butyl are encompassed by the term "alkyl." Specifically included within the definition of "alkyl" are those aliphatic hydrocarbon chains that are optionally substituted.

The carbon number as used in the definitions herein refers to carbon backbone and carbon branching, but does not include carbon atoms of the substituents, such as alkoxy substitutions and the like.

The term "alkenyl", as used herein, whether used alone or as part of another group, refers to a substituted or unsubstituted aliphatic hydrocarbon chain and includes, but is not limited to, straight and branched chains having 2 to 8 carbon atoms and containing at least one double bond. Preferably, the alkenyl moiety has 1 or 2 double bonds. Such alkenyl moieties may exist in the E or Z conformations and the compounds of this invention include both conformations. Specifically included within the definition of "alkenyl" are those aliphatic hydrocarbon chains that are optionally substituted. Heteroatoms, such as O, S or N—R, attached to an alkenyl should not be attached to a carbon atom that is bonded to a double bond.

"Aryl" as used herein, employed alone or in combination with other terms, refers to an optionally substituted, mono-, di-, tri-, or other multicyclic aromatic ring system having from about 6 to about 20 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl.

"Akoxy," as used herein, employed alone or in combination with other terms, refers to the group R—O— where R is an alkyl group, as defined herein.

The term "alkoxyalkoxy", as used herein, whether used alone or as part of another group, refers to the group Ra—O—Ra—O—, where Ra is an alkyl group, as defined herein.

The term "alkoxyalkyl" as used herein, employed alone or in combination with other terms, refers to an alkyl, as herein defined, substituted by an alkoxy group, as herein defined. An example of an alkoxyalkyl moiety is methoxyethyl.

"Alkoxycarbonyl," as used herein, employed alone or in combination with other terms, refers to the group R—O—C(=O)— where R is an alkyl group of 1 to 6 carbon atoms.

The term "alkylalkoxy", whether used alone or as part of another group, refers to an alkyl group, as defined herein, substituted with an alkoxy group, as defined herein.

The term "alkylaryl", as used herein, whether used alone or as part of another group, refers to the group —Rb—Ra, where Rb is an aryl group, as defined herein, substituted by Ra, an alkyl group as defined herein.

"Akylthio," as used herein, employed alone or in combination with other terms, refers to the group R—S— where R is an alkyl group, as defined herein.

"Alkynyl," as used herein, employed alone or in combination with other terms, refers to an alkyl group of at least two carbon atoms having one or more triple bonds, wherein alkyl is as defined herein. Alkynyl groups can be optionally substituted.

The term "arylalkyl", employed alone or in combination with other terms, is defined herein as, unless otherwise stated, an aryl, as herein defined, suitably substituted on any open ring position with an alkyl moiety wherein the alkyl chain is either a ($C_1$-$C_6$) saturated hydrocarbon moiety. Examples of arylalkyl moieties include, but are not limited to, chemical groups such as benzyl, 1-phenylethyl, 2-phenylethyl, diphenylmethyl, 3-phenylpropyl, 2-phenylpropyl, fluorenylmethyl, and homologs, isomers, and the like.

"Aryloxy," as used herein, employed alone or in combination with other terms, refers to the group R—O— where R is a aryl group, as defined herein.

"Cycloalkyl," as used herein, employed alone or in combination with other terms, refers to an optionally substituted, alkyl group having one or more rings in their structures having from 3 to about 20 carbon atoms (and all combinations and subcombinations of ranges and specific numbers of carbon atoms therein), with from 3 to about 10 carbon atoms being preferred. Multi-ring structures may be bridged or fused ring structures. Groups include, but are not limited to, cyclopropyl, cyclobutyl, cyclopentyl, cyclohexyl, cyclooctyl, 2-[4-isopropyl-1-methyl-7-oxa-bicyclo[2.2.1]heptanyl], 2-[1,2,3,4-tetrahydro-naphthalenyl], and adamantyl.

The term halogen, employed alone or in combination with other terms, includes bromine, chlorine, fluorine, and iodine.

"Heteroaryl," as used herein, employed alone or in combination with other terms, refers to an optionally substituted, mono-, di-, tri-, or other multicyclic aromatic ring system that includes at least one, and preferably from 1 to about 4 sulfur, oxygen, or nitrogen heteroatom ring members. Heteroaryl groups can have, for example, from about 3 to about 20 carbon atoms (and all combinations and subcombinations of ranges and specific numbers of carbon atoms therein), with from about 4 to about 10 carbons being preferred. Non-limiting examples of heteroaryl groups include, for example, pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl. Substituents include those discussed above for aryl groups.

"Heteroaryloxy," as used herein, employed alone or in combination with other terms, refers to the group R—O— where R is a heteroaryl group, as defined herein.

The term "hydroxyalkyl", employed alone or in combination with other terms, is defined herein as, unless otherwise stated, an alkyl, as herein defined, substituted by an hydroxy group.

An optionally substituted alkyl, alkenyl, alkynyl, aryl, phenyl, or heteroaryl may be substituted with one or more substituents. Suitable optional substituents may be selected independently from nitro, cyano, —N($R_{15}$)($R_{16}$), halo, hydroxy, carboxy, alkyl, alkenyl, alkynyl, cycloalkyl, aryl, heteroaryl, alkoxy, aryloxy, heteroaryloxy, alkylalkoxy, alkoxycarbonyl, alkoxyalkoxy, perfluoroalkyl, perfluoroalkoxy, arylalkyl, alkylaryl, hydroxyalkyl, alkoxyalkyl, alkylthio, —S(O)$_2$—N($R_{15}$)($R_{16}$), —C(=O)—N($R_{15}$)($R_{16}$), ($R_{15}$)($R_{16}$)N-alkyl, ($R_{15}$)($R_{16}$)N-alkoxyalkyl, ($R_{15}$)($R_{16}$)N-alkylaryloxyalkyl, —S(O)$_s$-aryl (where s is an integer from 0 to 2) or —S(O)$_s$-heteroaryl (where s is an integer from 0 to 2). In certain embodiments of the invention, preferred substituents for alkyl, alkenyl, alkynyl and cycloalkyl include nitro, cyano, —N($R_{15}$)($R_{16}$), halo, hydroxyl, aryl, heteroaryl, alkoxy, alkoxyalkyl, and alkoxycarbonyl. In certain embodiments of the invention, preferred substituents for aryl and heteroaryl include —N($R_{15}$)($R_{16}$), alkyl, halo, perfluoroalkyl, perfluoroalkoxy, arylalkyl and alkylaryl. $R_{15}$ and $R_{16}$ are defined independently, as hydrogen or alkyl.

When alkyl or alkenyl moieties are substituted, for example, they may typically be mono-, di-, tri- or persubstituted. Examples for a halogen substituent include 1-bromo vinyl, 1-fluoro vinyl, 1,2-difluoro vinyl, 2,2-difluorovinyl, 1,2,2-trifluorovinyl, 1,2-dibromo ethane, 1,2 difluoro ethane, 1-fluoro-2-bromo ethane, $CF_2CF_3$, $CF_2CF_2CF_3$, and the like.

The compounds of the present invention exert their desirable action by blocking interleukin-1β (IL-1β) induced nuclear factor κB (NF-κB) luciferase reporter activity, or interleukin-6 (IL-6) expression in an ER dependent fashion in human endothelial cells. Certain compounds appear to show no proliferative effects on uterine and breast tissue associated with estrogen in vivo. This lack of estrogen side effects appears to be confirmed in vitro by the lack of expression of creatine kinase (CK), a classic estrogen responsive gene. Such compounds are expected to prove useful for the treatment and prevention of chronic inflammatory diseases without stimulating uterine and breast cell proliferation as found with classic estrogens Those skilled in the art will recognize that numerous synthetic routes are provided to the compounds of the instant invention. Among such routes are those involving:
  a) providing a chiral, non-racemic α-alkyl substituted benzylalcohol of the general structure (II)

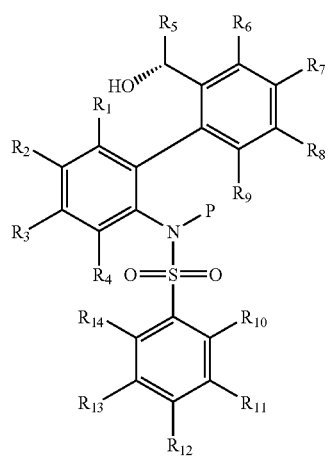

(II)

wherein P is hydrogen or an amino protecting group, such as methoxyethyl(trimethylsilyl) or methoxyethoxymethyl.
  b) removing the optional amino protecting group P; and
  c) cyclizing the chiral alcohol (II) to the desired compound (I) by reacting with an alkyl or arylphosphine such as triphenylphosphine and a diaryl or dialkylazodicarboxylate such as diethyl- or di-tert-butyl-azodicarboxylate in an aprotic solvent such as tetrahydrofuran at temperatures ranging from ambient to 70° C.

The chiral alcohol of general structure (II) may be conveniently obtained by reduction of the corresponding ketone of general structure (III)

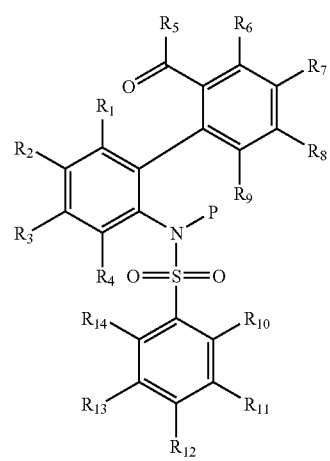

(III)

with a suitable chiral reducing agent such as (S)-tetrahydro-1-methyl-3,3-diphenyl-1H,3H-pyrrolo[1,2-c][1,3,2]oxazaborole and borane-methyl sulfide complex or [(+)-B-chlorodiisopinocampheylborane].

Another embodiment of the present invention provides synthetic methods for the preparation of a chiral compound of formula I comprising of the steps of
  a) providing the achiral phenanthridine of general structure (IV),

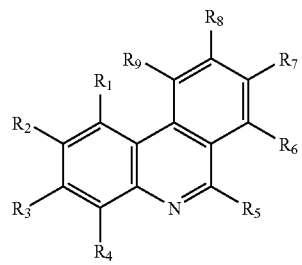

(IV)

b) mixing (IV) with an arylsulfonyl chloride of general structure (V) in dichloromethane or toluene

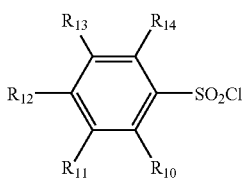

(V)

c) adding the mixture from step (b) to a suitable chiral reducing agent such as (R)-tetrahydro-1-methyl-3,3-diphenyl-1H,3H-pyrrolo[1,2-c][1,3,2]oxazaborole and borane methyl sulfide complex at room temperature.

Another embodiment of the present invention provides for the preparation of the chiral compound of general structure (I) wherein $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ are defined as hereinbefore, comprising contacting a compounds of formula (VI)

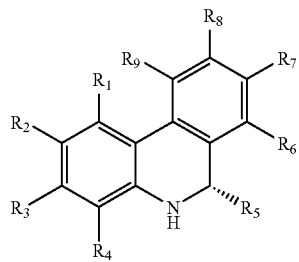
(VI)

with an arylsulfonyl chloride of formula (V)

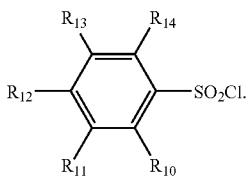
(V)

In an embodiment of the present invention the chiral compounds having formula (VI)

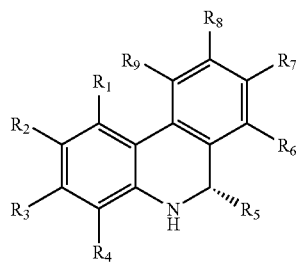
(VI)

are conveniently prepared by reduction of the compounds having formula (IV)

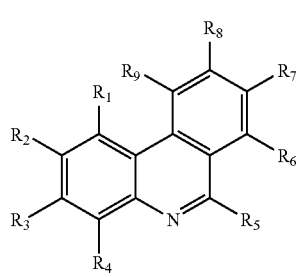
(IV)

with a chiral sodium triacyloxyborohydride reducing agent.

In another embodiment of the present invention the chiral compounds having formula (VI)

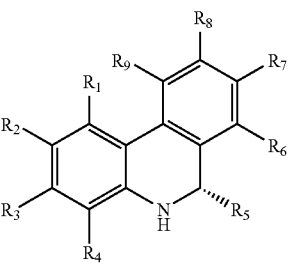
(VI)

are prepared by reduction of the compounds having formula (IV)

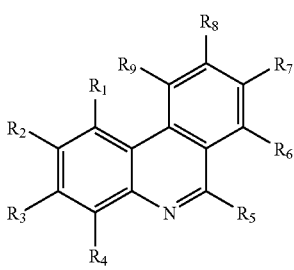
(IV)

with a chiral reducing agent in the presence of a metal borohydride and a halotrialkylsilane.

The present invention also provides methods of treating atherosclerosis, myocardial infarction, congestive heart failure, arthritis and inflammatory bowel disease in humans or other mammals. Such methods generally comprise administering to a human or other mammal an effective amount of a compound of the present invention.

It is understood that the effective dosage of the active compounds of this invention may vary depending upon the particular compound utilized, the mode of administration, the condition, and severity thereof, of the condition being treated, as well as the various physical factors related to the individual being treated. For treating atherosclerosis, myocardial infarction, congestive heart failure, arthritis and/or inflammatory bowel disease, generally satisfactory results may be obtained when the compounds of this invention are administered to the individual in need at a daily dosage of from about 0.1 mg to about 1 mg per kilogram of body weight, preferably administered in divided doses two to six times per day, or in a sustained release form. For most large mammals, the total daily dosage is from about 3.5 mg to about 140 mg, preferably from about 3.5 to about 5 mg. In the case of a 70 kog human adult, the total daily dose will generally be from about 7 mg to about 70 mg and may be adjusted to provide the optimal therapeutic result.

The tablets, pills, capsules, and the like may also contain a binder such as gum tragacanth, acacia, corn starch or gelatin: excipients such as dicalcium phosphate; a disintegrating agent such as corn starch, potato starch, aloinic acid; a lubricant such as magnesium stearate; and a sweetening agent such as sucrose, lactose or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elexir may contain, in addition to the active ingredients, sucrose as a sweetening agent, methyl and propyl parabens as preservatives, a dye and a flavoring such as cherry or orange flavor.

These active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy injectability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Representative Synthetic Processes

According to the preferred process of Scheme I, 2-iodoaniline was converted to the sulfonamide (VII) by treatment with 4-methoxybenzenesulfonyl chloride in the presence of an organic base such as triethylamine or pyridine in an aprotic solvent, such as dichloromethane. The sulfonamide was protected with a nitrogen protecting group, such as methoxyethyl(trimethylsilyl). The protected intermediate (VIII) was then transformed into the corresponding arylboronic acid (IX) by treatment with an organometallic reagent, like n-butyllithium, followed by a trialkyl boronate, such as trimethyl or triisopropyl boronate. The arylboronic acid (IX) was then coupled with 2-bromo-5-fluoroacetophenone (vida infra) using a palladium (0) catalyst preferably tetrakis (triphenylphosphine)palladium (0) and an inorganic base, such as sodium hydroxide, sodium carbonate, or potassium carbonate. The resulting ketone (X) was reduced with enantiomeric control using a chiral reducing agent such as (S)-tetrahydro-1-methyl-3,3-diphenyl-1H,3H-pyrrolo[1,2-c][1,3,2]oxazaborole and borane-methyl sulfide complex. Removal of the nitrogen protecting group from the resulting benzyl alcohol (XI) to give (XIII) followed by ring closure to (XIII) employing standard Mitsunobu conditions, and final removal of the oxygen protecting group provided the desired compound (I) wherein $R_7$ is fluorine, $R_5$ is methyl, and $R_{12}$ is methoxy.

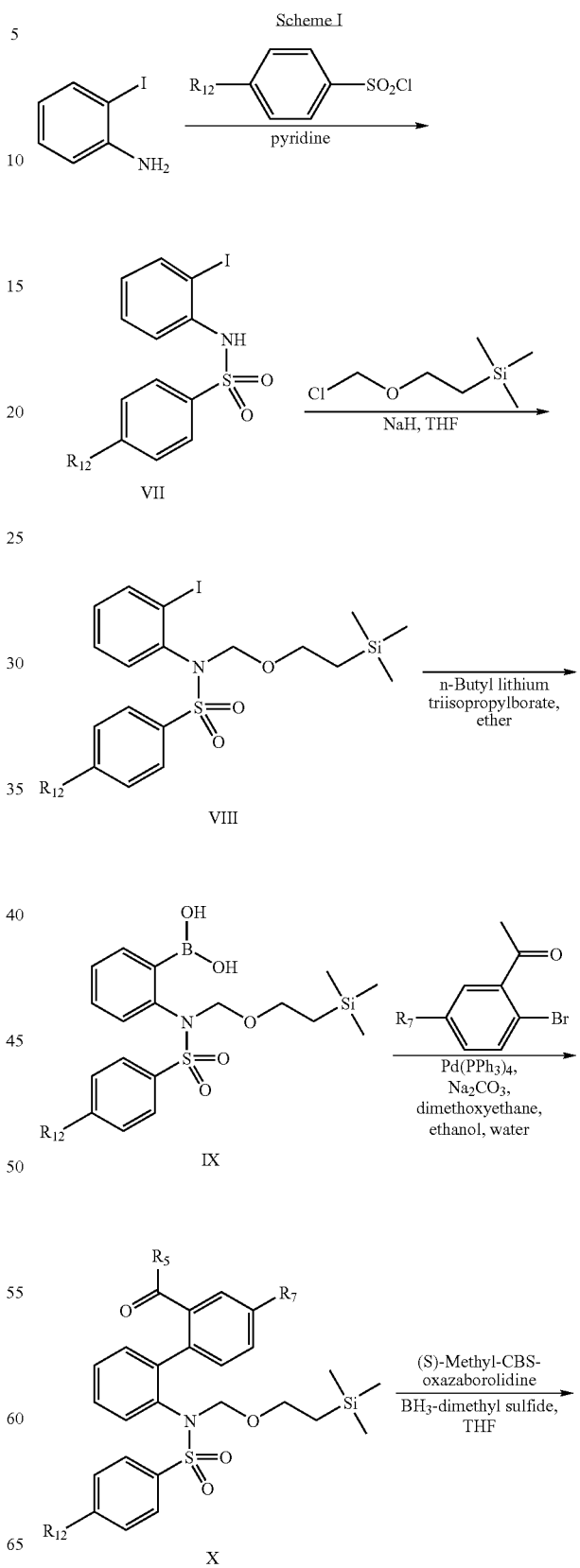

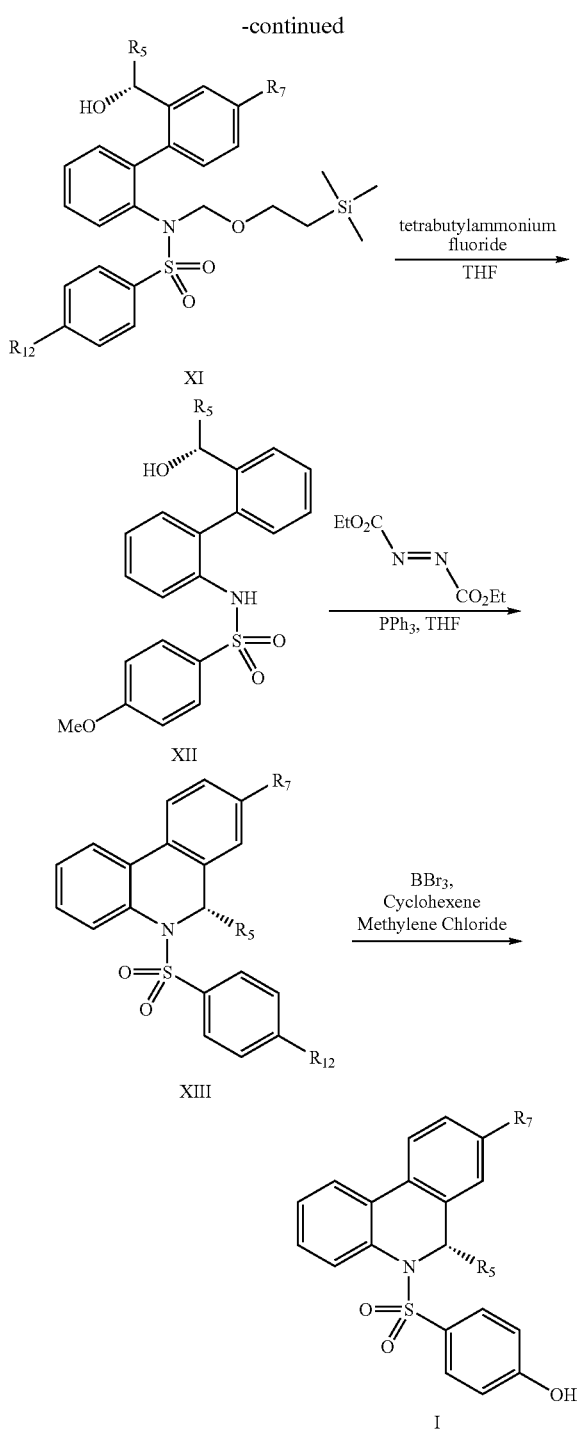

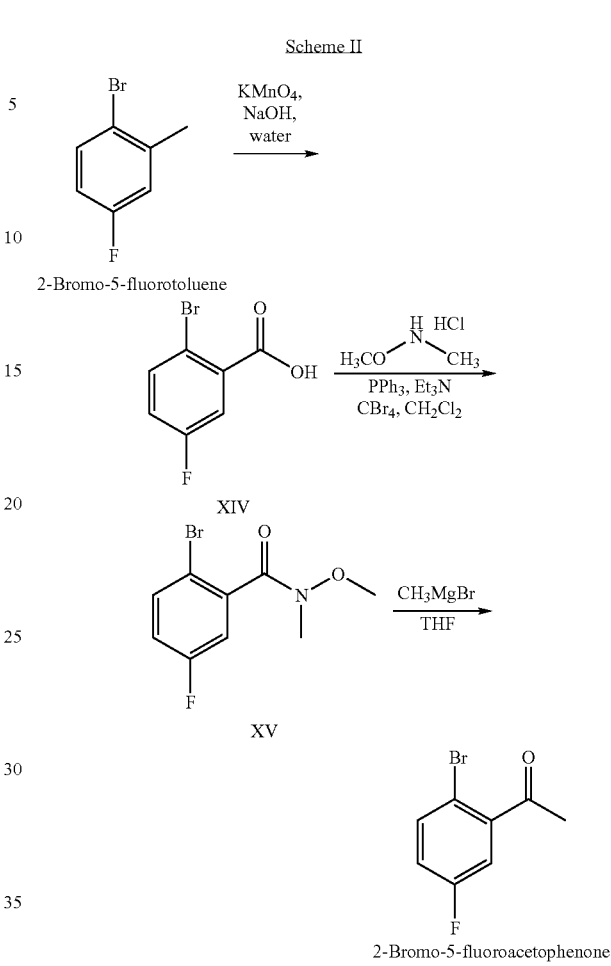

2-Bromo-5-fluoroacetophenone, which is a reactant in the formation of the intermediate ketone (X, R₇=F) above was prepared essentially according to a published procedure (see PCT Patent Applications WO 95/16682 and WO 00/77010) as shown in Scheme II. Thus the benzoic acid (XIV) obtained by oxidation of 2-bromo-5-fluorotoluene was transformed into the Weinreb amide (XV) by using standard peptide synthesis protocols followed by treatment of the Weinreb amide (XV) with methyl magnesium bromide to furnish 2-bromo-5-fluoroacetophenone.

A related, alternate process for the preparation of compound I wherein $R_7$ is hydrogen, is shown in Scheme III. 2-Bromoaniline was converted to the sulfonamide (XVI) by treatment with 4-methoxybenzenesulfonyl chloride in the presence of an organic base such as triethylamine or pyridine, in an aprotic solvent, such as dichloromethane. The sulfonamide and the arylboronic acid (XVII) were coupled using a palladium (0) catalyst preferably tetrakis(triphenylphosphine)palladium (0) and an inorganic base, such as sodium hydroxide, sodium carbonate, or potassium carbonate. The ketone (XVIII) was then reduced with enantiomeric control using a chiral reducing agent such as (S)-tetrahydro-1-methyl-3,3-diphenyl-1H,3H-pyrrolo[1,2-c][1,3,2]oxazaborole and borane-methyl sulfide complex. The resulting benzyl alcohol (XIX) was cyclized onto the sulfonamide using standard Mitsunobu conditions, and finally the oxygen protecting group of (XM) was removed to furnish the desired compound (I), wherein $R_7$ is hydrogen, $R_5$ is methyl, and $R_{12}$ is hydroxy.

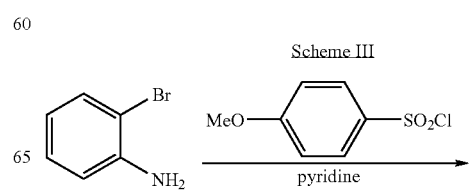

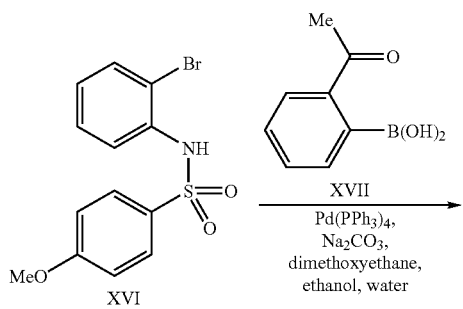

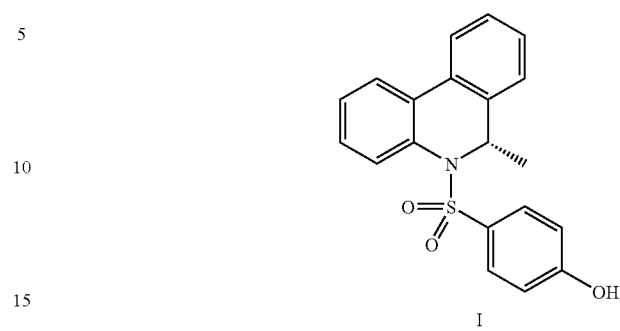

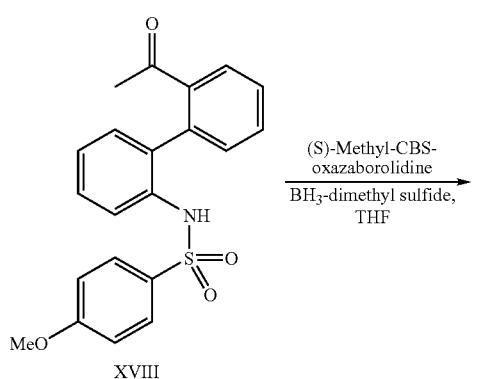

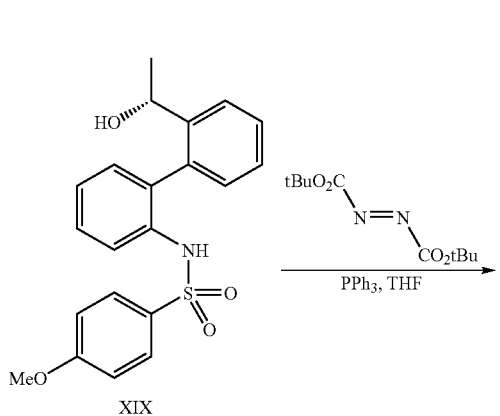

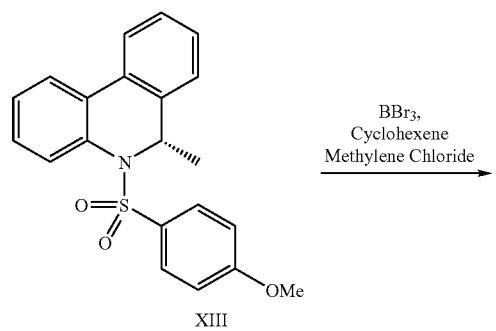

Alternatively, compound (I) wherein $R_7$ is fluorine, can also be synthesized by the method shown in Scheme IV. The appropriately substituted phenanthridine (XX) and the sulfonyl chloride were added as a dichloromethane solution to the chiral reducing agent to furnish directly the desired (S)-8-fluoro-5-[(4-methoxyphenyl)sulfonyl]-6-methyl-5,6-dihydrophenanthridine (XIII). Removal of the oxygen protecting group afforded the desired product (I) wherein $R_7$ is fluorine, $R_5$ is methyl, and $R_{12}$ is hydroxy.

Scheme IV

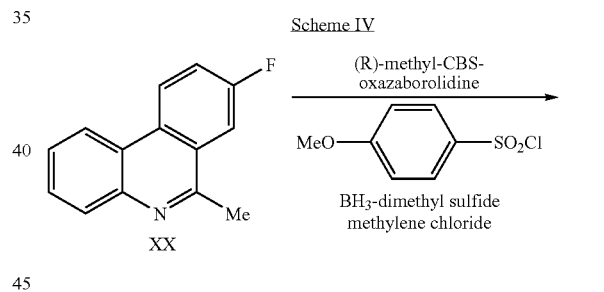

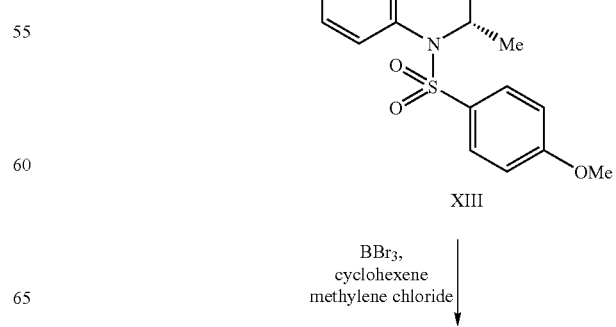

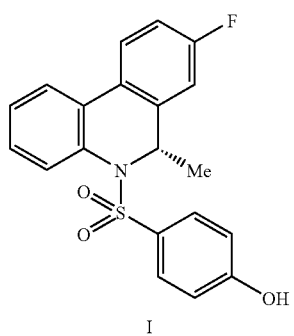

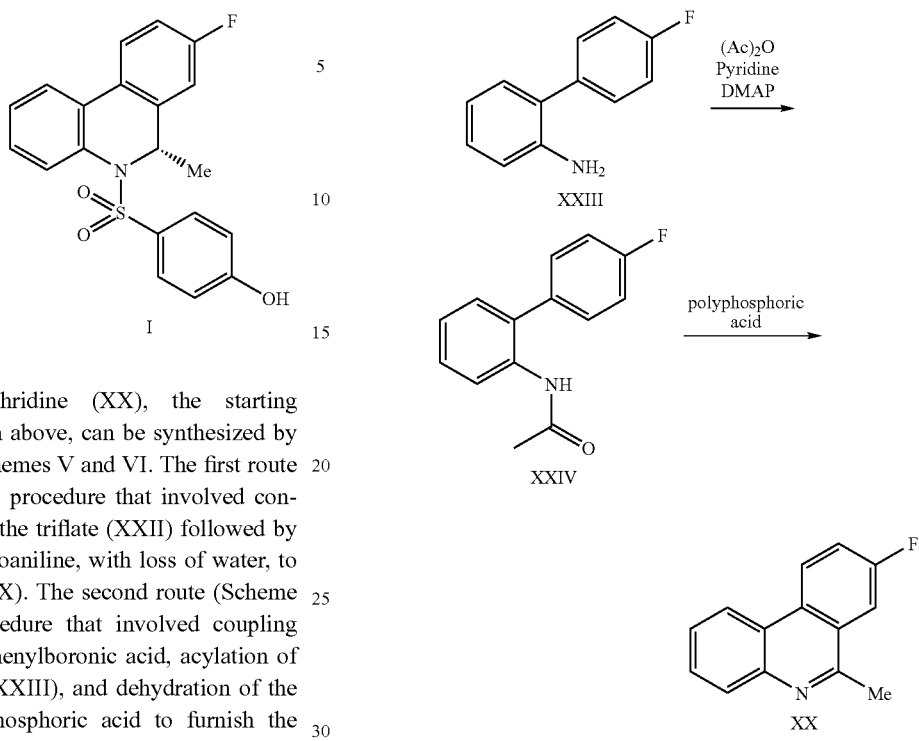

8-Fluoro-6-methylphenanthridine (XX), the starting material for synthesis shown above, can be synthesized by the following alternative Schemes V and VI. The first route (Scheme V) was a two step procedure that involved converting the phenol (XXI) to the triflate (XXII) followed by coupling the triflate to 2-iodoaniline, with loss of water, to form the desired product (XX). The second route (Scheme VI) was a three step procedure that involved coupling 2-iodoaniline and 4-fluorophenylboronic acid, acylation of the resulting biaryl amine (XXIII), and dehydration of the amide (XXIV) with polyphosphoric acid to furnish the desired product (XX).

Another preferred process is illustrated in Scheme VII. It was found that the desired compound (I) where $R_7$ is fluorine, can be synthesized in two steps and with high degree of enantioselectivity by the asymmetric reduction of the phenanthridine (XX) of Scheme VI with various chiral sodium triacyloxyborohydrides as reducing agents (see: K. Yamada, *Chem. Pharm. Bull.*, 31, 70 (1983) and *J. Chem. Soc. Perkin Trans. I*, 265 (1983)), preferably with sodium (S)-hydrotris[1-(2-methylpropyl)1,2-pyrrolidinedicarboxylato-$O^2$]borate(1-) [prepared from sodium borohydride and (S)-N-isobutyloxycarbonylproline according to the procedure of S. Atarashi et al., *J. Heterocyclic Chem.*, 28, 329 (1991)] in an aprotic solvent such as dichloronmethane. The resulting chiral dihydrophenanthridine (XXV) was then reacted with a suitably substituted phenylsulfonyl chloride to provide the sulfonamide (XIII). Enantiomeric excess was enhanced by recrystallization from a suitable solvent system preferably, toluene:ethanol (3:7, v/v). Deprotection in the manner of Scheme III yielded (I) wherein $R_7$ is fluorine, $R_5$ is methyl and $R_{12}$ is OH.

Scheme V

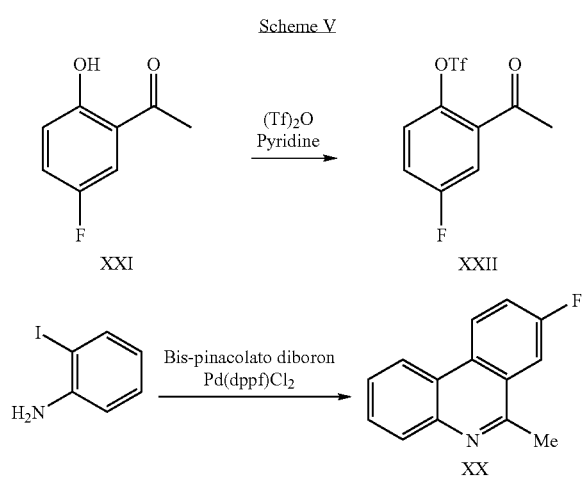

Scheme VI

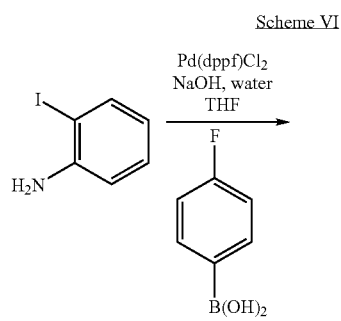

Scheme VII

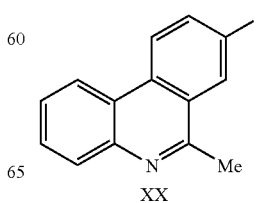
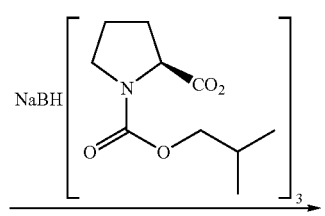

-continued

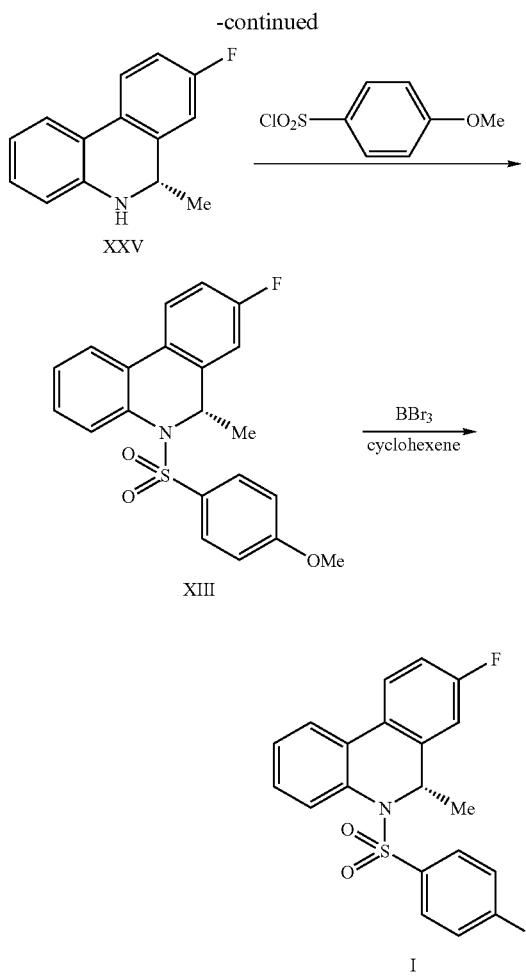

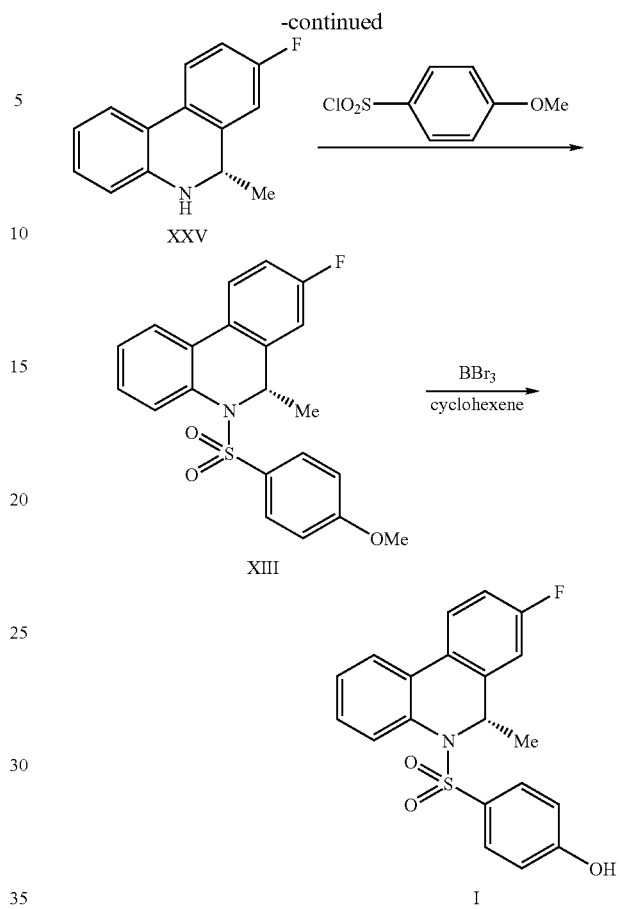

Alternatively, it was found (Scheme VIII) that a high degree of enantioselectivity in the reduction of the appropriately substituted phenanthridine (XX) is also achieved with a chiral reducing agent such as (R)-tetrahydro-1-methyl-3,3-diphenyl-1H,3H-pyrrolo[1,2-c][1,3,2]oxazaborole and a metal borohydride, preferably lithium or sodium borohydride in the presence of a halotrialkylsilane, preferably chlorotrimethylsilane (see: A. Giannis and K. Sandhoff, *Angew. Chem. Int. Ed. Engl.*, 28, 218 (1989)), in an aprotic solvent such as mixtures of toluene, tetrahydrofuran and dichloromethane. The dihydrophenanthridine (XXV) is then converted to the desired compound (I) wherein $R_5$ is methyl, $R_7$ is fluorine, and $R_{12}$ is OH by the steps outlined in Scheme VII.

Scheme VIII

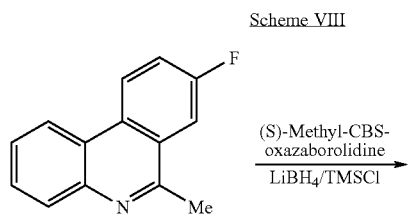

The compounds of this invention were evaluated in the following standard pharmacological test procedures which demonstrated the anti-inflammatory activity for the compounds of this invention. The test procedure used and the results obtained are briefly described below.

In Vitro Test Procedures

Cells

T-175 flasks of 100% confluent HAECT-1 cells (immortalized human aortic endothelial cells) were washed with 8 mL of HBSS (HEPES buffered saline solution) and infected for four hours with 6 mL of a 1:10 dilution of Ad5-wt-hERα virus (an adenovirus transfection vector that mediates CMV promoter driven expression of human ERα) in phenol red free Endothelial Cell Basal medium (Clonetics, San Diego Calif., Catalog #CC-3129) containing 0.25% bovine serum albumin (EBM-BSA). After four hours, the cells were washed with EBM-BSA and incubated overnight in the same medium. Following overnight incubation, the cells were washed with EBM-BSA and infected for 2 hours with 6 mL of a 1:10 dilution of Ad5-3×(NFκB). Luc virus (Adenovirus luciferase expression vector driven by 3 repeats of the MHC NFκb site 5' to the thymidine kinase promoter) in EBM-BSA. After two hours, the cells were washed and incubated at 34° C. for 1 hour. The cells were then washed, trypsinized, counted and resuspended in 95% FBS/5% dimethylsulfoxide at a concentration of 4×10⁶ cells/mL, frozen as 1 or 5 mL aliquots in cryo-vials and stored at −150° C. Control (no ER infection) cells were processed as above without Ad5-wt-hERα virus infection.

IL-6 And Creatine Kinase Test Procedure

ERα infected HAECT-1 cells or control cells were thawed, diluted 42× in warm EBM-BSA, plated into 96-well plates at 0.1 mL/well and incubated for 4 h at 34° C. Test compounds were added to the cells as 2× stocks in EBM-BSA containing 2 ng/mL IL-1β (R&D Systems) and plates were returned to the incubator (34° C.). After 15-20 h, 100 µL aliquots of media were removed from the cells and assayed for IL-6 content using a BioSource human IL-6 ELISA Kit. Cells were subsequently washed with 300 µL of Dulbecco's phosphate buffered saline and lysed in 50 µL of Cell Culture Lysis Reagent (Promega). Luciferase was determined on a Wallac Victor$^2$ Luminometer (Gaithersburg, Md.) using 10 µL of lysate and mixing with 100 µL of Promega Luciferase Assay reagent. Creatine kinase was determined from the rate of increase in $A_{340}$ following addition of 100 µL of CK assay reagent (Sigma, cat. No 47-10) to the remainder of the cell lysate.

Data Analyses

For $IC_{50}$ and $EC_{50}$ calculations, mean IL-6, luciferase or CK values versus $\log_{10}$ of the compound concentration were fitted to a four parameter logistic equation. The $IC_{50}/EC_{50}$ value, 'Hill slope', upper and lower limits of the curve were iteratively estimated.

Mice

Ovariectomized C57BL/6 mice (16-20 g) (Taconic) were separated into groups of 8. After 5-7 days of recuperation, the mice were fed a chow diet or an atherogenic diet (15.75% fat, 1.25% cholesterol and 0.5% sodium cholate) (Purina diet #21539). EE or test compound was administered once daily by gavage in a methylcellulose/tween vehicle (0.1 ml per mouse) for 5 weeks. At the end of the experimental period, the liver was collected and uterine wet weight was recorded.

RNA Analysis

Liver total RNA was prepared by using Trizol reagent (BRL). Estrogen and compound regulation of NF-κB target genes were verified by real time RT-PCR using an ABI PRISM 7700 Sequence Detection System according to the manufacturer's protocol (Applied Biosystems). The data was analyzed using the Sequence Detector v1.7 software (Applied Biosystems) and normalized to GAPDH using the Applied Biosystems primer set.

In Vitro Results

Table 1 summarizes the results obtained for the compound of example 8 contained herein and its enantiomer in the HAECT-1 NF-κB, IL-6 and creatine kinase assays in Ad5-wt-ER infected cells and are compared to the results obtained for the same compounds in the HAECT-1 NF-κB and creatine kinase assays in uninfected cells.

TABLE 1

Effects of 17-β-estradiol on NF-κB, IL-6 and CK expression in Ad5-wt-ER infected HAECT-1 cells

| Compound | NF-κB | | IL-6 | | CK | |
|---|---|---|---|---|---|---|
| | $IC_{50}$ (nM) | Efficacy (%)* | $IC_{50}$ (nM) | Efficacy (%)* | $IC_{50}$ (nM) | Efficacy (%)* |
| E2 | 1 | 100 | 1.7 | 100 | 5.8 | 100 |
| Ent-Example 8** | 1826 | 81 | | | Inactive | |
| Example 8 | 59 | 99 | 303 | 118 | Inactive | |

*Efficacy values are relative to the maximal inhibition (NF-κB or IL-6 assay) or stimulation (CK assay) observed with E2;
**The enantiomer example 8.

E2 inhibits NF-κB and IL-6 expression in Ad5-wt-ER infected HAECT-1 cells with an $IC_{50}$ value around 1 M and induces expression of creatine kinase in the same cells with similar potency (5.8 nM) (Table 1). In contrast, compounds of the present invention potently and efficaciously inhibit NF-κB and IL-6 expression in Ad5-wt-ER infected HAECT-1 cells but do not induce CK expression (Table 1) in an ER-dependent manner. The ability of compounds of the present invention to inhibit NF-κB and IL-6 expression without inducing CK activity (Table 1) is consistent with an anti-inflammatory activity in the absence of classic estrogenic activity.

In Vivo Activity

Treatment with the test compounds did not appear to result in a significant induction in uterine wet weight increase, an undesirable activity associated with EE (Table 2).

TABLE 2

Effects of EE (0.01 mg/kg/day) and test compound (10 mg/kg/day) on uterine wet weight increase in C57BL/6 compared to vehicle control.

| | Uterine Wet Weight Increase | |
|---|---|---|
| Compound | Fold Increase | Efficacy (%) |
| EE | 5.0 | 100 |
| ent-Example 8** | 0 | 0 |
| Example 8 | 0 | 0 |

**The enantiomer of example 8

These results suggest an anti-inflammatory role for the test compounds in terms of their ability to block inflammatory gene expression, with the desired selectivity in activity since no induction in uterine wet weights was observed.

The following examples are presented to illustrate rather than limit the scope of the present invention.

EXAMPLE 1

N-(2-Iodophenyl)-4-methoxybenzenesulfonamide

To a stirred solution of 2-iodoaniline (24.82 g, 113.3 mmol) in anhydrous pyridine (36 mL) was added 4-methoxybenzenesulfonyl chloride (23.42 g, 113.3 mmol). The dark solution was heated at 80° C. for one hour. The reaction mixture was evaporated in vacuo and the residue was poured onto an ice/water mixture. The aqueous phase was decanted and the oily residue was triturated several times with 150 mL portions of water. The resulting solid was collected by filtration and washed with water and hexane. The crude material was dried under a stream of air for three hours. Recrystallization from ethanol afforded tan crystals of the title compound (39.0 g, 81.71 mmol, 72%). An analytically pure sample was prepared by recrystallization from acetone.

MS [(-ESI), m/z]: 388 [M–H]⁻;

$^1$H NMR (500 MHz, DMSO-d$_6$) δ9.54 (d, J=8.2 Hz, 1H), 7.82 (dd, J=7.8, 1.4 Hz, 1H), 7.62 (d, J=8.9 Hz, 2H), 7.29 (t, J=7.4 Hz, 1H), 7.07 (d, J=9.0 Hz, 2H), 7.00 (d, J=7.9 Hz, 1H), 6.95 (t, J=7.6 Hz, 1H), 3.81 (s, 3H);

Anal. calcd for C$_{13}$H$_{12}$INO$_3$S: C 40.12, H 3.11, N 3.60. Found: C 40.01, H 3.07, N 3.73.

EXAMPLE 2

N-(2-Iodophenyl)-4-methoxy-N-{[2-(trimethylsilyl)ethoxy]methyl}benzenesulfonamide To a stirred suspension of sodium hydride (1.17 g, 29.25 mmol, 60% in oil) in anhydrous tetrahydrofuran (40 mL), which had been cooled to 0° C., was added N-(2-iodophenyl)-4-methoxybenzenesulfonamide (9.36 g, 19.6 mmol) in tetrahydrofuran (20 mL). After the addition was complete, the cooling bath was removed and the mixture stirred at room temperature for 90 minutes. 2-(Trimethylsilyl)ethoxymethyl chloride (4.25 g, 25.5 mmol) in tetrahydrofuran (20mL) was added dropwise and the reaction mixture stirred for an additional 16 hours. Water (10 mL) was added and the mixture was concentrated in vacuo. The residue was partitioned between ethyl acetate and water. The organic phase was washed with a saturated, aqueous sodium chloride solution. After drying over anhydrous magnesium sulfate, the organic phase was filtered and the filtrate was evaporated in vacuo to yield the crude title compound as a colorless oil. Purification by silica gel chromatography by elution with hexane-ethyl acetate (10:1) provided the title compound as a colorless oil. Trituration with hexane provided the title compound as a white solid (8.55 g, 16.5 mmol, 84%), m.p. 69-70° C.

MS [(ESI) m/z]: 537 [M+NH$_4$]⁺;

$^1$H NMR (500 MHz, DMSO-d$_6$) δ7.94 (d, J=7.9 Hz, 1H), 7.65 (d, J=8.9 Hz, 2H), 7.37 (t, J=7.6Hz, 1H), 7.09-7.14 (m, 3H), 6.94 (d,J=7.9Hz, 1H), 5.18 (d, J=11.1 Hz, 1H), 4.66 (d, J=11.0 Hz, 1H), 3.84 (s, 3H), 3.44-3.51 (m, 2H), 0.77 (m, 2H), –0.08 (s, 9H);

Anal. calcd for C$_{19}$H$_{26}$INO$_4$SSi: C 43.93, H 5.04, N 2.70. Found: C 43.75, H 4.98, N 2.59.

EXAMPLE 3

2-([[(4-Methoxyphenyl)sulfonyl]{[2-(trimethylsilyl)ethoxy]methyl}amnino)phenylboronic acid A stirred solution of N-(2-iodophenyl)-4-methoxy-N-{[2-(trimethylsilyl)ethoxy]methyl}benzenesulfonamide (8.50 g, 16.4 mmol) in anhydrous diethyl ether (125 mL) under argon was cooled to –78° C. and a solution of 2.5 N butyllithium in hexanes (7.85 mL, 19.6 mmol) was added dropwise by syringe over two minutes. Triisopropyl borate (5.6 mL, 24 mmol) was added and the reaction mixture was warmed to room temperature. After 30 minutes, the reaction mixture was cooled to 0° C. and 1 N hydrochloric acid was added (10 mL). The mixture was diluted with ethyl acetate. The organic layer was washed with both water and a saturated, aqueous sodium chloride solution. After drying over anhydrous magnesium sulfate, the organic phase was filtered and the filtrate was evaporated in vacuo to yield the crude title compound as a colorless oil. Purification by silica gel column chromatography, eluting with hexane-ethyl acetate (3:1 to 2:1), afforded the title compound as a colorless oil (6.50 g, 14.9 mmol, 91%).

MS [(ESI) m/z]: 436 [M–H]⁻;

$^1$H NMR (500 MHz, DMSO-d$_6$) δ7.82 (m, 2H), 7.58 (d, J=7.2 Hz, 1H), 7.54 (d, J=8.9 Hz, 2H), 7.25-7.32 (m, 2H), 7.05 (d, J=7.9 Hz, 2H), 6.69 (d, J=7.6 Hz, 1H), 5.01 (s, 2H), 3.83 (s, 3H), 3.49 (t, J=8.4 Hz, 2H), 0.81 (t, J=8.2 Hz, 2H), –0.06 (s, 9H);

Anal. calcd for C$_{19}$H$_{28}$BNO$_6$SSi•0.10 C$_6$H$_{14}$: C 52.78, H 6.64, N 3.14. Found: C 53.03, H 6.43, N 3.23.

EXAMPLE 4

N-(2'-Acetyl-5'-fluoro-1,1'-biphenyl-2-yl)-4-methoxy-N-{[2-(trimethylsilyl)ethoxy]methyl}benzenesulfonamide To a solution of 2-([[(4-methoxyphenyl)sulfonyl]{[2-(trimethylsilyl)ethoxy]methyl}amino) phenylboronic acid (3.31 g, 7.57 mmol) and tetrakis(triphenylphosphine) palladium (0) (0.87 g, 0.76 mmol) in dimethoxyethane (30 niL) under argon was added 1-(2-bromo-5-fluorophenyl)ethanone (1.86 g, 8.57 mmol) in ethanol (1 mL). Aqueous sodium carbonate (2 M, 40 mL) was added and the reaction mixture was heated at 90° C. for 14 hours. The solvent was removed in vacuo and the residue was partitioned between water and ethyl acetate. The organic layer was washed with water and a saturated, aqueous sodium chloride solution. After drying over anhydrous magnesium sulfate, the organic phase was filtered and the filtrate was evaporated in vacuo to yield the crude title compound as an oil. Purification by silica gel column chromatography by elution with hexane-ethyl acetate (5:1) gave the title compound as a pale yellow oil, which crystallized on standing (2.22 g, 4.19 mmol, 55%), m.p. 94-95° C.

MS [(ESI), m/z]: 528 [M–H]⁻;

$^1$H NMR (500 MHz, DMSO-d$_6$) δ7.70 (s, J=7.0 Hz, 1H), 7.64 (d, J=8.9 Hz, 2H), 7.59 (m, 1H), 7.44 (m, 1H), 7.34 (m, 2H), 7.18 (d, J=7.2 Hz, 1H), 7.12 (d, J=8.6 Hz, 2H), 6.92 (d, J=7.6 Hz, 1H), 4.40-4.90 (m, 2H), 3.86 (s, 3H), 3.14 (m, 2H), 2.27 (s, 3H), 0.64 (m, 2H), –0.13 (s, 9H);

Anal. calcd for C$_{27}$H$_{32}$FNO$_5$SSi: C, 61.22 H, 6.09 N, 2.64. Found: C 61.12, H, 6.01, N 2.44.

EXAMPLE 5

N-{4'-Fluoro-2'-[(1R)-1-hydroxyethyl]-1,1'-biphenyl-2-yl}-4-methoxy-N-{[2-(trimethylsilyl)ethoxy]methyl}benzenesulfonamide To a solution of (R)-2-methyl-CBS-oxazaborolidine (0.11 mL, 1.0 M in toluene, 0.11 mmol) and borane-methyl sulfide complex (0.067 mL, 10 M in dimethyl sulfide, 0.67 mmol) at 0° C. under argon was added N-(2'-acetyl-5'-fluoro-1,1'-biphenyl-2-yl)-4-methoxy-N- {[2-(trimethylsilyl)ethoxy]methyl} benzenesulfonamide (0.30 g, 0.56 mmol) in dichloromethane (5 mL) dropwise over 30 minutes. The solution was warmed to room temperature and stirred for four hours. The solution was cooled to 0° C., water was added, and the mixture was warmed to room temperature and stirred for 30 minutes. The solution was cooled to 0° C. and hydrochloric acid (1 mL, 1 N aqueous) was added. The mixture was stirred for one hour. The solution was extracted with diethyl ether (3×20 mL). The combined organic layers were washed with water and brine and dried over anhydrous magnesium sulfate. The mixture was passed through a pad of silica gel (5:1 hexane:ethyl acetate) to yield the title compound as a yellow oil (0.286 g, 96%). The $^1$H NMR spectrum was consistent with a 1:1 mixture of rotamers.

MS [(–ESI), m/z]: 590 [M+CH$_3$CO$_2$]$^-$;

$^1$H NMR (500 MHz, DMSO-d$_6$) δ –0.15 (s, 9H, Si—CH$_3$), 3.85 (s, 3H, O—CH$_3$)

Anal. calcd for C$_{27}$H$_{34}$FNO$_5$SSi: C 60.99, H 6.45, N 2.63. Found: C 61.28, H 6.56, N 2.39.

EXAMPLE 6

N-{4'-Fluoro-2'-[(R)-1-hydroxyethyl]-1,1'-biphenyl-2-yl}-4-methoxybenzenesulfonamide N-{4'-Fluoro-2'-[(R)-1-hydroxyethyl]-1,1'-biphenyl-2-yl}-4-methoxy-N-{[2-(trimethylsilyl)ethoxy]methyl}benzenesulfonamide (0.28 g, 0.51 mmol) was dissolved in tetrahydrofuran (10 mL) and tetrabutylammonium fluoride in tetrahydrofuran (1.0 M, 0.76 mL, 0.76 mmol) was added. The solution was heated at reflux for six hours. The solution was concentrated in vacuo and the mixture was dissolved in ethyl acetate and washed with water. The solution was dried over anhydrous magnesium sulfate and the solvent was removed in vacuo. The product was passed through a silica gel plug (5:1 hexane: ethyl acetate followed by 1:1 hexane:ethyl acetate) to yield the title compound as a solid (0.135 g, 66%), m.p. 137-138° C. The NM spectrum of the title compound was consistent with rotamers. The peaks attributed to individual rotamers in the $^1$H NMR spectrum coalesced at 90° C.

MS [(–ESI), m/z]: 400 [M–H]$^-$;

$^1$H NMR (500 MHz, DMSO-d$_6$) δ 9.06 (s, 0.4H), 8.70 (s, 0.6H), 7.63 (d, J=8.7 Hz, 0.8H), 7.47 (d, J=8.6 Hz, 1.2H), 7.32 (m, 4H), 7.16 (d, J=4.0 Hz, 1.2H), 7.01 (m, 2.2H), 6.90 (t, J=8.4 Hz, 0.6H), 6.77 (t, J=5.8 Hz, 0.4H), 6.42 (t, J=5.8 Hz, 0.6H), 5.15 (m, 0.6H), 5.03 (m, 0.4H), 4.44 (m, 0.4H), 4.26 (q, J=6.3 Hz, 0.6H), 3.82 (s, 3H), 1.15 (d, J=6.3 Hz, 1.25H), 1.11 (d, J=6.3 Hz, 1.75H);

Anal. calcd for C$_{21}$H$_{20}$FNO$_4$S: C 62.83, H 5.02, N 3.49. Found: C 62.75, H 4.93, N 3.41.

EXAMPLE 7

(S)-8-Fluoro-5-[(4-methoxyphenyl)sulfonyl]-6-methyl-5,6-dihydrophenanthridine N-{4'-fluoro-2'-[(1R)-1-hydroxyethyl]-1,1'-biphenyl-2-yl}-4-methoxybenzene-sulfonamide (0.12 g, 0.29 mmol) and triphenylphosphine (0.31 g, 1.2 mmol) were dissolved in tetrahydrofuran (10 mL) and diethylazodicarboxylate (0.21 g, 0.19 mL, 1.2 mmol) was added. The solution was stirred overnight at room temperature. The solution was concentrated in vacuo and the mixture was dissolved in ethyl acetate and washed with water. The organic phase was dried over anhydrous magnesium sulfate, filtered, and concentrated in vacuo. The crude product was purified by flash chromatography on silica gel (3:1 hexane: ethyl acetate) to yield the title compound as a crystalline solid (0.085 g, 79%), m.p. 181-182° C.

Chiral stationary phase HPLC analysis (Chiralpak AD-25×5 cm column) on a Rainin Auto-Prep System using 90:10 hexane:isopropanol as the eluding solvent with a 1 mL/min flow rate showed this compound to be 99.6% optically pure. The first peak was the title compound.

Rt (major, S enantiomer)=9.5 min

Rt (minor, R enantiomer)=12.1 min;

[α]$_D^{25}$ =+251.80 (c=1% solution, CHCl$_3$);

MS [(+ESI), m/z]: 384 [M+H]$^+$;

$^1$H NMR (500 MHz, DMSO-d$_6$) δ 7.75 (dd, J=7.7, 1.1 Hz, 1H), 7.61 (m, 1H), 7.48 (dd, J=8.6, 5.4 Hz, 1H), 7.43 (m, 1H), 7.38 (m, 1H), 7.16 (dd, J=9.2, 2.8 Hz, 1H), 6.98-6.92 (m, 3H), 6.59 (d, J=8.8 Hz, 2H), 5.43 (q, J=7.0 Hz, 1H), 3.64 (s, 3H), 1.13 (d, J=7.0 Hz, 3H).

*The absolute configuration was determined by single crystal x-ray analysis.

EXAMPLE 8

4-[(S)-8-Fluoro-6-methyl-6H-phenanthridine-5-sulfonyl]-phenol (S)-8-Fluoro-5-(4-methoxy-benzenesulfonyl)-6-methyl-5,6-dihydrophenanthridine (1.26 g, 3.29 mmol) was suspended in cyclohexene (6.0 mL, 59 mmol). Boron tribromide (20 mL, 1.0 M solution in dichloromethane) was added dropwise at room temperature. The solution was stirred for 20 hours. A solution of saturated, aqueous sodium bicarbonate (300 mL) was added dropwise and then the mixture was extracted with dichloromethane (6×20 mL). The combined organic layers were dried over anhydrous sodium sulfate, filtered, and concentrated in vacuo. The crude material was purified by silica gel flash chromatography (1:19 to 1:4 ethyl acetate:hexane) and then recrystallization (dichloromethane-hexane) to afford the title compound as white crystals (1.1 g, 90%), m.p. 193° C.

[α]$_D^{25}$=+267.20 (c=1% solution, CHCl$_3$);

MS [(–ESI), m/z]: 368 [M–H]$^-$;

$^1$H NMR (500 MHz, DMSO-d$_6$) δ 10.24 (br s, 1 H), 7.76 (dd, J=7.6, 1.5 Hz, 1H), 7.60 (dd, J=7.8, 1.4 Hz, 1H), 7.52 (dd, J=8.7,5.0 Hz, 1H), 7.41 (m, 1H), 7.37 (m, 1H), 7.17 (dd, J=9.2, 2.7 Hz, 1H), 6.96 (td, J=8.7, 2.7 Hz, 1H), 6.86 (d, J=8.9 Hz, 2H), 6.38 (d, J=8.9 Hz, 2H), 5.41 (q, J=7.0 Hz, 1H), 1.13 (d, J=7.0 Hz, 3H);

Anal. calcd for C$_{20}$H$_{16}$FNO$_3$S: C 65.03, H 4.37, N 3.79. Found: C 64.82, H 4.47, N 3.71.

EXAMPLE 9

N-(2'-Acetyl-biphenyl-2-yl)-4-methoxy-benzenesulfonamide

N-(2-Bromo-phenyl)4-methoxy-benzenesulfonamide (0.34 g, 0.99 mmol) was dissolved in dimethoxyethane (4 mL) and tetrakis(triphenylphosphine)palladium (0) (0.23 g, 0.2 mmol) was added. 2-acetylphenylboronic acid (0.16 g, 0.99 mmol), dissolved in ethanol (1 mL), was added, followed by aqueous sodium carbonate (4.2 mL, 2 M). The reaction mixture was heated at 100° C. for 14 hours. The mixture was diluted with a saturated, aqueous sodium chloride solution (200 mL) and extracted with dichloromethane (4×30 mL). The combined organic extracts were dried over anhydrous sodium sulfate, filtered, and concentrated in vacuo to yield a residue. The crude product was purified by silica gel chromatography (1:9 to 3:7 ethyl acetate:hexane) to afford the title product.

$^1$H NMR (400 MHz, DMSO-d$_6$) δ 9.20 (s, 1H), 7.76-7.00 (m, 10H), 6.89 (d, 2H), 3.81 (s, 3H), 2.14 (s, 3H).

EXAMPLE 10

N-[(R)-2'-(1-Hydroxy-ethyl)-biphenyl-2-yl]-4-methoxy-benzenesulfonamide

N-(2'-Acetyl-biphenyl-2-yl)-4-methoxy-benzenesulfonamide was dissolved in dichloromethane (5 mL) and added dropwise to a separate, stirring solution of (S)-2-methyl-CBS-ozazaborolidine (0.1 mL, 1.0 M solution in toluene) and borane-methyl sulfide complex (0.06 mL, 10 M solution in methyl sulfide) that had been cooled to −20° C. The mixture was stirred for five hours at −20° C., warmed to −5° C., and stirred for an additional 36 hours. Methanol (20 mL) was added and then removed in vacuo (×3). The crude product was purified by silica gel chromatography (1:9 to 2:3 ethyl acetate:hexane) to afford the product (0.05 g, 26% from N-(2-bromo-phenyl)-4-methoxy-benzenesulfonamide) as a mixture of rotamers.

$^1$H NMR (400 MHz, DMSO-d$_6$) δ8.95 (s, 0.3H), 8.61 (s, 0.7H), 7.59 (m, 1.7H), 7.39 (m, 2.3H), 7.32 (m, 1.3H), 7.18 (m, 2H), 7.06 (m, 1.7H), 6.99 (m, 2H), 6.74 (dd, 0.3H), 6.32 (dd, 0.7H), 5.1 (br s, 0.7H), 4.91 (br s, 0.3H), 4.46 (q, 0.3H), 4.25 (q, 0.7H), 3.83 (s, 3H), 1.15 (m, 3H).

EXAMPLE 11

(S)-5-(4-Methoxy-benzenesulfonyl)-6-methyl-5,6-dihydrophenanthridine

N-[(R)-2'-(1-Hydroxy-ethyl)-biphenyl-2-yl]-4-methoxy-benzenesulfonamide (0.04 g, 0.10 mmol) was dissolved in tetrahydrofuran (10 mL) and cooled to 0° C. Di-tert-butylazodicarboxylate (0.05 g, 0.21 mmol) and triphenylphosphine (0.06 g, 0.21 mmol) were added. After four hours, additional di-tert-butylazodicarboxylate (0.05 g, 0.21 mmol) and triphenylphosphine (0.06 g, 0.21 mmol) were added. The mixture was warmed to room temperature and stirred for 36 hours. Trifluoroacetic acid (2.5 mnL) was added and the mixture was stirred for two hours. A solution of saturated, aqueous sodium bicarbonate was added (100 niL) and the resulting mixture was extracted with diethyl ether (5×20 mL). The combined organic extracts were dried over anhydrous magnesium sulfate, filtered, and concentrated in vacuo to yield an oil. The resulting oil solidified upon standing. The title compound was evaluated by chiral stationary phase HPLC (Chiralpak AD-25×0.46 cm column) on a Rainin Auto-Prep System using 90:10 hexane:isopropanol as the eluding solvent with a 0.8 mL/min flow rate. HPLC analysis showed the product to be a 95:5 mixture of enantiorners where the S enantiomer was the major product.

Rt (major, S enantiomer)=9.7 min;

Rt (minor, R enantiomer)=11.9 min;

$^1$H NMR (400 MHz, DMSO-d$_6$) δ7.76 (dd, J=7.5, 1.8 Hz, 1H), 7.60 (m, 1H), 7.46-7.33 (m, 3H), 7.25-7.08 (m, 3H), 6.92 (d, J=8.9 Hz, 2H), 6.52 (d, J=8.9 Hz, 2H), 5.40 (q, J=7.0 Hz, 1H), 3.60 (s, 3H), 1.12 (d, J=7.0 Hz, 3H).

EXAMPLE 12

4-[(S)-6-Methyl-6H-phenanthridine-5-sulfonyl]-phenol

The title compound was prepared in the same manner as 4-[(S)-8-fluoro-6-methyl-6H-phenanthridine-5-sulfonyl]-phenol (example 8) using boron tribromide (1 M solution in dichloromethane) and cyclohexene.

EXAMPLE 13

(S)-8-Fluoro-5-[(4-methoxyphenyl)sulfonyl]-6-methyl-5,6-dihydrophenanthridine A solution of 8-fluoro-6-methylphenanthridine (0.5 g, 2.4 mmol) and 4-methoxybenzenesulfonyl chloride (0.514 g, 2.49 mmol) in dichloromethane (5 mL) was added to a solution of borane-methyl sulfide (0.142 mL, 1.42 mmol, 10 M solution in methyl sulfide) and (R)-2-methyl-CBS-oxazaborolidine (0.47 mL, 0.4734 mmol, 1.0 M solution in toluene) in dry dichloromethane (6 mL) over the course of three hours at room temperature. The reaction mixture was stirred for twelve hours and then a solution of aqueous sodium hydroxide (10 mL, 1 N) was added. The aqueous layer was extracted with dichloromethane (3×). The organic layers were combined, washed with a solution of saturated, aqueous sodium chloride, and dried over anhydrous sodium sulfate. The organic solvent was removed in vacuo to yield the crude product as an orange solid. The crude product was purified by chromatography on silica gel (1:10 ethyl acetate:hexane) to afford the title compound as a white solid (0.489 g, 1.28 mmol, 54% ).

The title compound was evaluated by chiral stationary phase HPLC (Chiralpak AD-25×5 cm column) on a Rainin Auto-Prep System using 90:10 hexane:isopropanol as the eluding solvent with a 15 mL/min flow rate. Chiral stationary phase HPLC analysis showed the product to be a 90:10 mixture of enantiomers, $[α]_D^{25}$=+155.20 (c=1% solution, CHCl$_3$);

Rt (major, S enantiomer)=10.0 min;

Rt (minor, R enantiomer)=12.8 min;

MS [(+ESI) m/z]: 384 [M+H]$^+$;

$^1$H NMR (500 MHz, DMSO-d$_6$) δ7.75 (d, J=7.6 Hz, 1H), 7.60 (d, J=7.8 Hz, 1H), 7.49 (d, J=8.7 Hz, 1H), 7.44-7.36 (m, 2H), 7.17 (d, J=9.2 Hz, 1H), 6.97 (d, J=8.7 Hz, 2H), 6.93 (d, J=8.9 Hz, 1H), 6.59 (d, J=8.8 Hz, 2H), 5.43 (q, J=7.0 Hz, 1H), 3.64 (s, 3H), 1.13 (d, J=6.9 Hz, 3H);

Anal. calcd for C$_{21}$H$_{18}$FNO$_3$S 0.10 H$_2$O: C 65.78, H 4.73, N 3.65. Found: C 65.47, H 4.76, N 3.64.

EXAMPLE 14

2-Acetyl-4-fluorophenyl trifluoromethanesulfonate

Trifluoromethanesulfonic anhydride (8.6 mL, 51 mmol) was added dropwise at 0° C. to a stirring solution of 5'-fluoro-2'-hydroxy-acetophenone (6.4 g, 41 mmol) in pyridine (62 mL). The reaction was stirred overnight from 0° C. to ambient temperature. The reaction solution was diluted with diethyl ether (500 mL). The organic layer was washed with 1 N aqueous hydrochloric acid (1×300 mL), followed by a saturated, aqueous sodium chloride solution (2×300 mL), dried over anhydrous sodium sulfate, filtered, and concentrated in vacuo to give a maroon-colored liquid (11.9 g, 100% ). The product was further purified by Kugel-Rohr distillation to afford a yellow oil that solidified upon standing.

MS [(EI) m/z]: 286 [M]$^+$;

$^1$H NMR (500 MHz, DMSO-d$_6$) δ8.02 (dd, J=8.6, 2.9 Hz, 1H), 7.60-7.66 (m, 2H), 2.62 (s, 3H);

IR (neat) v: 3115, 3080, 1700, 1590, 1480, 1420, 1410, 1200, 1140, 860, 830 cm$^{-1}$;

Anal. calcd for C$_9$H$_6$F$_4$O$_4$S: C 37.77, H 2.11. Found: C 38.10, H 2.09.

EXAMPLE 15

8-Fluoro-6-methylphenanthridine

A solid mixture of 2-iodoaniline (5.1 g, 23 mmol), bis(pinacolato)diboron (6.4 g, 25 mmol), potassium acetate (7.4 g, 75 mmol), and [1,1'-bis(diphenylphosphino)ferrocene]dichloropalladium(II), complex with dichloromethane (1:1) (0.8 g, 0.9 mmol) was degassed (5×). N,N-Dimethylformamide (50 mL) was added to the reaction and the resulting dark brown suspension was degassed (5×). The reaction mixture was heated at 85° C. for two hours. The reaction was analyzed by
$^1$H NMR and TLC and no starting material was present (2-iodoaniline). 2-Acetyl-4-fluorophenyl trifluoromethanesulfonate (7.9 g, 28 mmol) was added to the reaction mixture, along with aqueous sodium carbonate (2 M, 61 mL, 122 mmol) and additional [1,1'-bis(diphenylphosphino)ferrocene]dichloropalladium(II), complex with dichloromethane (1:1) (1.0 g, 1.22 mmol) and N,N-dimethylformamide (50 mL). The reaction mixture was degassed several times and heated at 85° C. for 18 hours. The mixture was cooled to room temperature and poured into water (250 mL). The suspension was extracted with diethyl ether (2×250 mL). The combined organic extracts were dried over sodium sulfate, filtered, and concentrated in vacuo to give a brown oil. Purification by column chromatography (1:4 ethyl acetate:hexane) gave the product as a pale yellow solid (1.33 g, 27%).

MS [(+ESI), m/z]: 212 [M+H]$^+$;
$^1$H NMR (500 MHz, DMSO-d$_6$) δ8.90 (dd, J=9.0, 5.5 Hz, 1H), 8.72 (dd, J=8.0, 1.4 Hz, 1H), 8.07 (dd, J=10.1, 2.6 Hz, 1H), 8.00 (dd, J=8.0, 1.3 Hz, 1H), 7.79-7.84 (m, 1H), 7.64-7.75 (m, 2H), 2.93 (s, 3H);
Anal. calcd for C$_{14}$H$_{10}$FN: C 79.60, H 4.77, N 6.63. Found: C 79.39, H 4.93, N 6.52.

EXAMPLE 16

N-(4'-Fluorobiphenyl-2-yl)-acetamide

To a solution of 2-iodoaniline (32.6 g, 149 mmol) and 4-fluorobenzeneboronic acid (20.8 g, 149 mmol) in tetrahydrofuran (1.5 L) was added [1,1'-bis(diphenylphosphino)ferrocene]dichloropalladium (II) complex with dichloromethane (2.20 g, 2.69 mmol), followed by aqueous sodium hydroxide (60 mL, 5 N). The reaction mixture was heated at reflux for twelve hours, cooled to ambient temperature, and the tetrahydrofuran was removed in vacuo. Ethyl acetate (250 mL) and a saturated, aqueous sodium chloride (100 mL) solution were added. The organic and aqueous phases were separated and the aqueous phase was extracted with ethyl acetate (2×50 mL). The combined organic phases were dried over anhydrous magnesium sulfate, filtered, and concentrated in vacuo. The resulting brown oil was filtered through a plug of silica gel (1:4 ethyl acetate:hexane). After concentration in vacuo, the resulting, impure 4'-fluoro-biphenyl-2-ylamine was dissolved in dichloromethane (75 mL). Pyridine (27.7 mL, 343 mmol), acetic anhydride (15.5 mL, 164 mmol), and 4-(dimethylamino)pyridine (0.55 g, 4.5 mmol) were added. The mixture was allowed to stir at ambient temperature for twelve hours. A saturated, aqueous ammonium chloride (250 mL) solution was added and the layers were separated. The aqueous phase was extracted with dichloromethane (3×75 mL) and the combined organic phases were washed with 0.1 N hydrochloric acid (2×50 mL) and a solution of saturated, aqueous sodium bicarbonate (1×50 mL), dried over anhydrous sodium sulfate, filtered, and concentrated in vacuo to a brown oil. Toluene was added and removed in vacuo (×3) to afford a brown solid, that was recrystallized from ethyl acetate-hexane (19.0 g obtained). The mother liquor was concentrated and purified by flash chromatography on silica gel (1:4 ethyl acetate:hexane) to provide additional material (5.0 g). The resulting, pure title compound was a colorless, crystalline solid (24.0 g, 70%), m.p. 123-124° C.

MS [(ESI), m/z]: 230 [M+H]$^+$;
$^1$H NMR (500 MHz, DMSO-d$_6$) δ9.24 (s, 1H), 7.44-7.23 (m, 8H), 1.87 (s, 3H);
Anal. calcd for C$_{14}$H$_{12}$FNO: C 73.35, H 5.28, N 6.11. Found: C 73.09, H 5.20, N 5.89.

EXAMPLE 17

8-Fluoro-6-methylphenanthridine

N-(4'-Fluorobiphenyl-2-yl)-acetamide (18.5 g, 80.7 mmol) was mixed with polyphosphoric acid (250 g) and then heated to 120° C. with vigorous stirring for 48 hours. The hot reaction mixture was poured onto ice and stirred vigorously until homogeneous. Concentrated ammonium hydroxide was added until the pH >9. A white precipitate formed. The mixture was filtered and the white solid was dissolved in ethyl acetate (250 mL) and filtered. The filtrate was washed with saturated, aqueous sodium chloride, dried over anhydrous sodium sulfate, filtered, and reduced in vacuo to a brown solid. The solid was purified by recrystallization from ethyl acetate-hexane to afford 8-fluoro-6-methylphenanthridine as white crystals (15.9 g, 94%), m.p. 92-93° C.

MS [(ESI), m/z]: 212 [M+H]$^+$:
$^1$H NMR (500 MHz, CDCl$_3$) δ8.63 (dd. J=9.0, 5.4 Hz, 1H), 8.49 (dd, J=8.2. 1.0 Hz, 1H), 8.10 (dd, J=8.1, 1.1 Hz, 1H), 7.84 (dd, J=9.6, 2.6 Hz, 1H), 7.71 (m, 1H), 7.65-7.57 (m, 2H), 3.01 (s, 3H);
Anal. calcd for C$_{14}$H$_{10}$FN 0.10 H$_2$O: C 78.93, H 4.83, N 6.57. Found: C 78.90. H 4.57, N 6.58.

EXAMPLE 18

(S)-8-Fluoro-6-methyl-5,6-dihydrophenanthridine

To a stirred suspension of sodium borohydride (9.28 g, 0.245 mole) in anhydrous tetrahydrofuran (372 mL) kept under nitrogen at 0° C. was added dropwise a solution of (S)-N-isobutyloxycarbonylproline (160 g, 0.743 mole; prepared according to S. Atarashi et al., *J. Heterocyclic Chem.* 28, 329 (1991)) in anhydrous tetrahydrofuran (372 mL). After stirring the reaction mixture overnight at room temperature the solvent was removed to provide a solid foam (168 g). This material was dissolved in dichloromethane (272 mL), the solution was cooled to 0° C. and treated dropwise under nitrogen with a solution of 8-fluoro-6methylphenanthridine (17.3 g, 0.082 mole) in dichloromethane (100 mL). The progress of the reaction was monitored by NMR. After 4 days at room temperature conversion reached 50%. Additional solution of S-hydridotris[1-(2-methylpropyl) 1,2-pyrrolidinedicarboxylato-O$^2$]borate(1-) (freshly prepared from 4.7 g of sodium borohydride and 81.6 g of (S)-N-isobutyloxycarbonylproline as described above) in dichloromethane (150 mL) was added dropwise at 0° C. After 7 days at room temperature the conversion reached 100%. The reaction mixture was cooled to 0° C. and 10% aqueous citric acid was added dropwise (200 mL). The mixture was allowed to reach room temperature (over 80 minutes) and then it was diluted with ethyl acetate (1.2 L). The organic layer was washed with 10% aqueous citric acid, followed by saturated aqueous potassium dihydrogenphosphate (2×200 mL). The organic layer was divided in 3 portions and each portion was washed sequentially with 1:1 (v/v) saturated aqueous sodium bicarbonate/ water (2×400 mL), water (1×400 mL), 1:1 (v/v) saturated aqueous sodium bicarbonate/ water (2×400 mL), water (1×400 mL), and brine (1×400 mL) to remove the (S)-N-isobutyloxycarbonyl proline. The combined organic extracts were dried over anhydrous sodium sulfate and evaporated to dryness to give 26.57 g of a brown oil which was immediately used in the next step without further purification.

EXAMPLE 19

(S)-8-Fluoro-5-[(4-methoxyphenyl)sulfonyl]-6-methyl-5,6-dihydrophenanthridine

To a stirred solution of crude (S)-8-fluoro-6-methyl-5,6-dihydrophenanthridine from Example 18 (26.57 g) in dichloromethane (221 mL) kept under argon at 0° C. was added triethylamine (13.7 mL), followed by dropwise addition of a solution of 4-methoxyphenylsulfonyl chloride (16.9 g) in dichloromethane (126 mL). The reaction mixture was allowed to warm to room temperature and after stirring overnight, was diluted with ethyl acetate (600 mL). The solution was washed with saturated aqueous potassium dihydrogenphosphate (2×200 mL) and brine (1×200 mL), and dried over anhydrous sodium sulfate. Removal of the solvent provided a brown oil (37.86 g) which was filtered through a plug of flash silica gel (300 g) with 20% ethyl acetate in hexane to provide 27.3 g (86.9% ) of product, shown to be an 86:14 mixture of enantiomers. This material was dissolved in 136 mL of hot 30% toluene in ethanol (ca. 5 mL/g). The hot solution was seeded and allowed to slowly reach room temperature. The needles were collected, rinsed with 30% toluene in ethanol (4×3 mL) and then with hexane (2×20 mL), and dried to provide 15.5 g (49% based on (S)-8-fluoro-6-methyl-5,6-dihydrophenanthridine) of title compound, m.p. 181-185° C. The compound was analyzed by chiral stationary phase HPLC (Chiralpak AD-25×0.46 cm column) on a HP-1100 using 90:10 hexane-isopropanol as the mobile phase with a 1 mL/min flow rate. The analysis showed the material to be a 99.75 : 0.25 mixture of enantiomers, $[\alpha]_D^{25}$=+239.5 (c=1, CHCl$_3$)
Rt (major, S enantiomer)=9.284 min
Rt (minor, R enantiomer)=12.243 min
MS [(+)ESI, m/z]: 384.10 [M+H]$^+$
Anal. Calcd for C$_{21}$H$_{18}$FNO$_3$S: C 65.78, H 4.73, N 3.65. Found: C 65.44, H 4.70, N 3.44.

EXAMPLE 20

(S)-8-Fluoro-6-methyl-5,6-dihydrophenanthridine

To a stirred suspension of lithium borohydride (8.25 g, 0.378 mole) in a mixture of toluene (94.7 niL) and tetrahydrofuran (9.46 mL) kept under nitrogen and at 0° C. was added dropwise chlorotrimethylsilane (96.1 nmL). Additional tetrahydrofuran (30 mL) and toluene (105 mL) were added to rinse the glassware. (R)-2-methyl-CBS-oxazaborolidine (56.8 mL) was added dropwise at room temperature. The mixture was cooled to 0° C. and solid 8-fluoro-6-methylphenanthridine (40 g, 0.189 mole) was added in two portions over a 10 minute and 5 minute period, respectively. The cooling bath was removed, the flask walls rinsed with toluene (60 mL) and the brown slurry was stirred at room temperature. Aliquots were taken at regular intervals to monitor the progress of the reaction. After 8 days the conversion reached 97% . The reaction mixture was cooled to 0° C., treated dropwise with 10% aqueous citric acid (100 mL) under vigorous stirring to control foaming. Ethyl acetate was added (800 mL) followed by more 10% aqueous citric acid (300 mL) and then methanol (300 mL) to redissolve the precipitate. The layers were separated and the organic layer was washed with saturated aqueous sodium bicarbonate (100 mL) and brine (100 mL), dried over anhydrous sodium sulfate and evaporated to dryness to provide 38.4 g (95% yield) of the title compound.
MS [(+)ESI, m/z]: 214.08 [M+H]$^+$

EXAMPLE 21

(S)-8-Fluoro-5-[(4-methoxyphenyl)sulfonyl]-6-methyl-5,6-dihydrophenanthridine

The title compound was prepared according to the procedure of Example 19, starting from the (S)-8-Fluoro-6-methyl-5,6-dihydrophenanthridine of Example 20 (38.4 g) and 4-methoxyphenylsulfonyl chloride (37.2 g). The crude product (65.6 g) was purified by filtration over a flash silica gel plug (1 Kg) eluting with 20-25% hexane-ethyl acetate to provide 54.1 (78.4% yield) of product. The material (54.1 g) was recrystallized twice from hot 30% toluene in ethanol. The solution was seeded hot and allowed to cool to room temperature. After about 3 hours the crystalline solid was collected, rinsed with 30% toluene in ethanol (1×15 mL) and with hexane (2×15 mL), and dried to provide 27.1 g (39.3% yield based on (S)-8-fluoro-6-methyl-5,6-dihydrophenanthridine) of title compound. The compound was analyzed by chiral stationary phase HPLC (Chiralpak AD-25×0.46 cm column) on a HP1100 using 90:10 hexane-isopropanol as the mobile phase with a 1 mL/min flow rate. The analysis showed the material to be a 98.7:1.3 mixture of enantiomers, $[\alpha]_D$=+246.74 (c=1, CHCl$_3$)
Rt (major, S enantiomer)=7.854 min
Rt (minor, R enantiomer)=9.027 min
MS [(+)ESI, m/z]: 384.07 [M+H]$^+$

EXAMPLE 22

4-{[(6S)-8-Fluoro-6-methylphenanthridin-5(6H)-yl]sulfonyl}phenyl sulfamate

To a stirred solution of 4-{[(6S)-8-fluoro-6-methylphenanthridin-5(6H)-yl]sulfonyl}phenol (1.11 g, 3.0 mmol) in dimethyacetamide (10 mL), cooled to 0° C., was added sulfamoyl chloride (1.39 g, 12.0 mmol). The mixture was allowed to warm to room temperature and stirring continued for 16 hours. Water (100 mL) was added and a white precipitate deposited on the inside of the reaction vessel. The water was removed and the flask was washed with additional water. The white solid was dissolved in dichloromethane and purified by preparative liquid chromatography on a Biotage® 40 Mi column of prepacked silica gel (90 g), eluting with a gradient of 30% -50% methyl tert-butyl ether in hexane, to afford the title compound (1.16 g, 87% ) as a white solid, m.p.
m.p. 165.5-167.3° C.
MS [(+ESI), m/z]: 449 [M+H]$^+$;
MS [(−ESI), m/z]: 447 [M−H]$^-$;

HRMS [(+ESI), m/z]: 449.06289 [M+H]+. Calcd for $C_{20}H_{17}FN_2O_5S_2$: 449.06357;

$^1$H NMR (400 MHz, DMSO-$d_6$) δ 1.16 (d, J=7.0 Hz, 3H), 5.49 (q, J=7.0 Hz, 1H), 6.97 (m, 3H), 7.14 (ddd, J=9.2, 2.9, 2.5 Hz, 2H), 7.20 (dd, J=9.2, 2.7 Hz, 1H), 7.45 (m, 3H), 7.63 (dd, J=7.8, 1.3 Hz, 1H), 7.77 (dd, J=7.6, 1.7 Hz, 1H), 8.13 (s, 2H);

Anal. Calcd for $C_{20}H_{17}FN_2O_5S_2$: C, 53.56; H, 3.82; N, 6.25. Found: C, 53.47; H, 3.82; N, 6.10.

$[\alpha]_D^{25}$=+211 ° (c=10.0 g/mL, CHCl$_3$)

Preferred compounds of this invention are selective antiinflammatory compounds useful for the treatment and prevention of chronic inflammatory diseases without stimulating uterine and breast cell proliferation as found with classic estrogens.

Preferred compounds are useful in treating or inhibiting osteoporosis and in the inhibition of bone demineralization, which may result from an imbalance in a individual's formation of new bone tissues and the resorption of older tissues, leading to a net loss of bone. Such bone depletion results in a range of individuals, particularly in post-menopausal women, women who have undergone bilateral oophorectomy, those receiving or who have received extended corticosteroid therapies, those experiencing gonadal dysgenesis, and those suffering from Cushing's syndrome. Special needs for bone, including teeth and oral bone, replacement can also be addressed using these compounds in individuals with bone fractures, defective bone structures, and those receiving bone-related surgeries and/or the implantation of prosthesis. Preferred uses include the treatment or inhibition of osteoarthritis, hypocalcemia, hypercalcemia, Paget's disease, osteomalacia, osteohalisteresis, multiple myeloma and other forms of cancer having deleterious effects on bone tissues.

Preferred compounds of this invention are also active in the brain and are therefore useful for inhibiting or treating Alzheimer's disease, cognitive decline, decreased libido, senile dementia, neurodegenerative disorders, depression, anxiety, insomnia, schizophrenia, and infertility. Such compounds preferably are also useful in treating or inhibiting benign or malignant abnormal tissue growth including, glomerulosclerosis, prostatic hypertrophy, uterine leiomyomas, breast cancer, scleroderma, fibromatosis, endometriosis, endometrial cancer, polycystic ovary syndrome, endometrial polyps, benign breast disease, adenomyosis, ovarian cancer, melanoma, prostate cancer, cancers of the colon, CNS cancers, such as glioma or astioblastomia.

Preferred compounds of this invention are cardioprotective and are antioxidants, and are useful in lowering cholesterol, triglycerides, Lp(a), and LDL levels; inhibiting or treating hypercholesteremia, hyperlipidemia, cardiovascular disease, atherosclerosis, peripheral vascular disease, restenosis, and vasospasm, and inhibiting vascular wall damage from cellular events leading toward immune mediated vascular damage.

Preferred uses also include treating disorders associated with inflammation or autoimmune diseases, including inflammatory bowel disease (Crohn's disease, ulcerative colitis, indeterminate colitis), arthritis (rheumatoid arthritis, spondyloarthropathies, osteoarthritis), pleurisy, ischemia/reperfusion injury (e.g. stroke, transplant rejection, myocardial infarction, etc.), asthma, giant cell arteritis, prostatitis, uveitis, psoriasis, multiple sclerosis, systemic lupus erythematosus and sepsis.

Additional representative uses of preferred compounds include treating or inhibiting ocular disorders including cataracts, uveitis, and macular degeneration and in treating skin conditions such as aging, alopecia, and acne.

Compounds of this invention are also useful in treating or inhibiting metabolic disorders such as type-II diabetes, of lipid metabolism, appetite (e.g. anorexia nervosa and bulimia); in treating or inhibiting bleeding disorders such as hereditary hemorrhagic telangiectasia, dysfunctional uterine bleeding, and combating hemorrhagic shock; and/or in disease states where amenorrhea is advantageous, such as leukemia, endometrial ablations, chronic renal or hepatic disease or coagulation diseases or disorders.

All patents, publications, and other documents cited herein are hereby incorporated by reference in their entirety.

What is claimed:

1. A method of synthesizing a compound of formula (I):

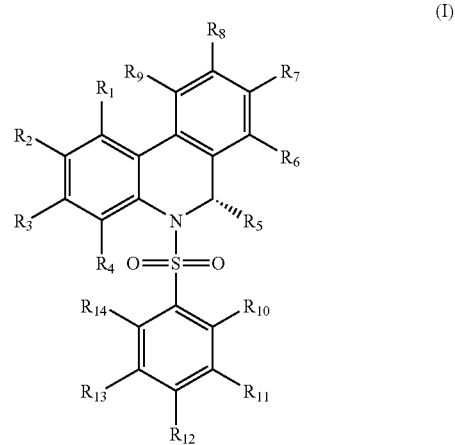

wherein:
$R_1$, $R_2$, $R_3$, $R_4$, $R_6$, $R_7$, $R_8$, $R_9$, $R_{10}$, $R_{13}$ and $R_{14}$ are, independently, hydrogen, $C_1$-$C_{12}$ alkyl, halogen, or $C_6$-$C_{10}$ aryl;

$R_5$ is $C_1$-$C_{12}$ alkyl or $C_6$-$C_{10}$ aryl; and $R_{11}$ and $R_{12}$ are, independently, hydrogen, $C_1$-$C_{12}$ alkyl, or —O—PG$_1$ where PG$_1$ is hydrogen, a phenol protecting group, sulfamate, or alkylcarbonate;

comprising:
providing chiral, non-racemic compound of formula (IIa):

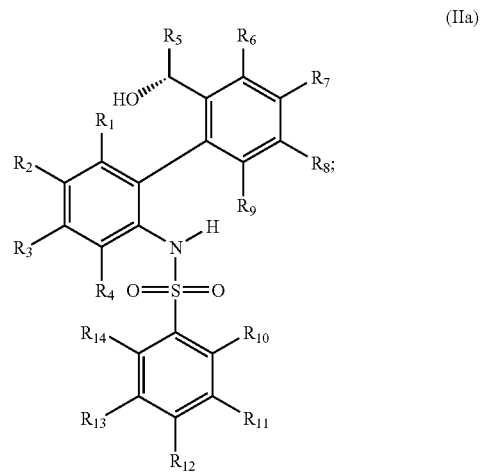

and
reacting said compound of formula (IIa) with an alkylphoshine or arylphosphine and a diarylazodicarboxylate or dialkylazodicarboxylate in an aprotic solvent to form the compound of formula (I), wherein said providing chiral, non-racemic compound of formula (IIa) optionally comprises:
(a) providing chiral, non-racemic compound of formula (II)

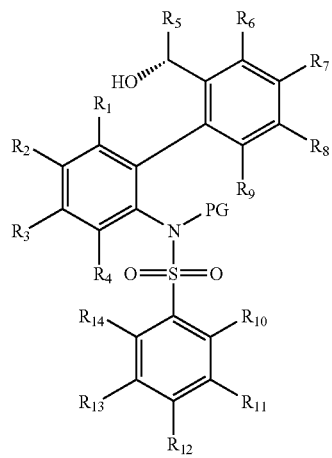

wherein PG is an amino protecting group; and
(b) removing said amino protecting group thereby forming the compound of formula (IIa).

2. The process of claim 1 wherein said reacting step is performed in tetrahydrofuran at a temperature from ambient to 70° C.

3. The process of claim 1 wherein said alkylphosphine or arylphosphine is triphenylphosphine.

4. The process of claim 1 wherein said diaryl or dialkylazodicarboxylate is a dialkylazodicarboxylate.

5. The process of claim 4 wherein said dialkylazodicarboxylate is diethyl- or di-ter-butylazodicarboxylate.

6. The process of claim 1 wherein $R_1$, $R_2$, $R_3$, $R_4$, $R_6$, $R_8$, $R_9$, $R_{10}$, $R_{11}$, $R_{13}$ and $R_{14}$ are each hydrogen.

7. The process of claim 6 where $R_5$ is methyl.

8. The process of claim 7 wherein $R_{12}$ is OH, $OCH_3$, sulfamate or alkylcarbonate.

9. The process of claim 8 wherein $R_7$ in $C_1$-$C_{12}$alkyl, C6-C10aryl, or fluoro.

10. The process of claim 1 wherein PG is an amino protecting group that is [2-(trimethylsilyl)ethoxy]methyl or methoxyethoxymethyl.

11. The process of claim 1 wherein said compound of formula (II) is obtained by reducing a compound of formula (III)

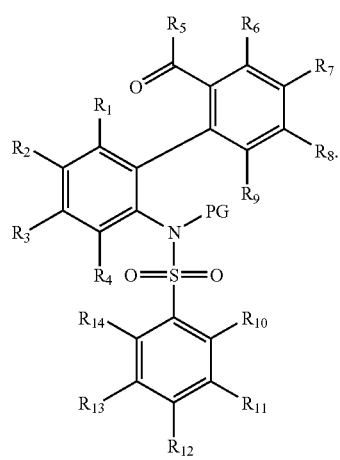

12. The method of claim 11 wherein said reduction is effected by reacting said compound having formula (III) with a chiral reducing agent and a borane methyl sulfide complex.

13. The process of claim 12 wherein said chiral reducing agent is (S)-tetrahydro-1-methyl-3,3-diphenyl-1H,3H-pyrrolo[1,2-c][1,3,2]oxazaborole or [(+)-B-chlorodiisopinocampheylborane].

14. The process of claim 1 wherein $R_5$ is methyl, $R_7$ is fluoro, $R_{11}$ is H and $R_{12}$ is —OP—$PG_1$.

15. The process of claim 1 further wherein $PG_1$ is a phenol protecting group, further comprising removing the phenol protecting group thereby converting —O—$PG_1$ to OH.

16. A method of synthesizing a compound of formula I:

(I)

[structure]

wherein:
$R_1$, $RR_2$, $R_3$, $R_4$, $R_6$, $R_7$, $R_8$, $R_9$, $R_{10}$, $R_{13}$ and $R_{14}$ are, independently, hydrogen, $C_1$-$C_{12}$ alkyl, halogen, or C6-C10aryl;
$R_5$ is $C_1$-$C_{12}$ alkyl or C6-C10 aryl; and
$R_{11}$ and $R_{12}$ are, independently, hydrogen or —O—$PG_1$ where $PG_1$ is hydrogen, or a phenol protecting group, sulfamate, or alkylcarbonate;

comprising:
forming an intermediate by reacting a compound of formula (IV)

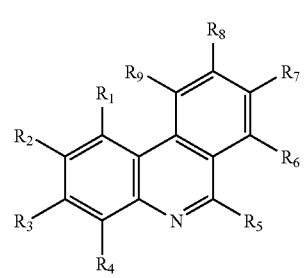

with an arylsulfonyl chloride of formula (V)

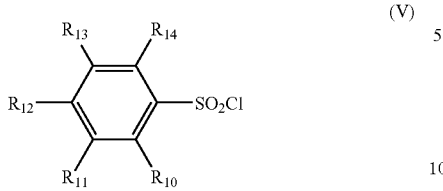

and reacting said intermediate with a chiral reducing agent and a borane methyl sulfide complex.

17. The process of claim 16 wherein said intermediate is formed in dichloromethane.

18. The process of claim 16 wherein said reducing agent is a (R)-tetrahydro-1-methyl-3,3-diphenyl-1H,3H-pyrrolo[1,2-c][1,3,2]oxazaborole.

19. The process of claim 16 wherein $R_1$, $R_2$, $R_3$, $R_4$, $R_6$, $R_8$, $R_9$, $R_{10}$, $R_{11}$, $R_{13}$ and $R_{14}$ are each hydrogen.

20. The process of claim 19 where $R_5$ is methyl.

21. The process of claim 20 wherein $R_{12}$ is OH, $OCH_3$, sulfamate, or alkylcarbonate.

22. The process of claim 21 wherein $R_7$ is $C_1$-$C_{12}$ alkyl, C6-C10 aryl, or fluoro.

23. The process of claim 16 wherein $R_5$ is methyl, $R_7$ is fluoro, $R_{11}$ is H and $R_{12}$ is —O—$PG_1$.

24. The process of claim 16 wherein $PG_1$ is a phenol protecting group, further comprising removing the phenol protecting group thereby converting —O—$PG_1$ to OH.

25. A method of synthesizing a compound of formula I:

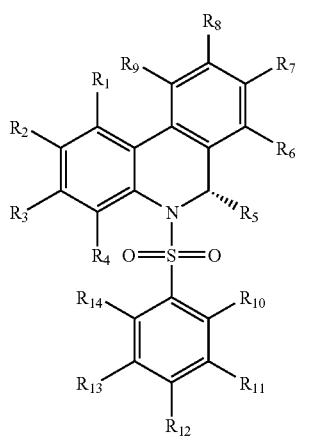

wherein:

$R_1$, $R_2$, $R_3$, $R_4$, $R_6$, $R_7$, $R_8$, $R_9$, $R_{10}$, $R_{13}$ and $R_{14}$ are, independently, hydrogen, $C_1$-$C_{12}$ alkyl, halogen, or C6-C10 aryl;

$R_5$ is $C_1$-$C_{12}$ alkyl or C6-C10 aryl; and $R_{11}$ and $R_{12}$ are, independently, hydrogen or —O—$PG_1$ where $PG_1$ is hydrogen, a phenol protecting group, sulfamate, or alkylcarbonate;

comprising:

reacting a compound of formula (a1)

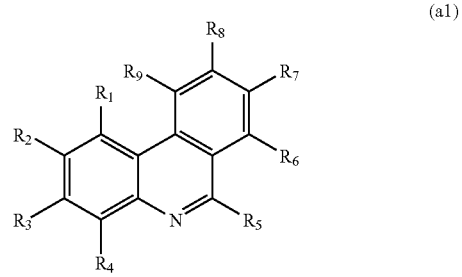

with a chiral reducing agent to produce an intermediate compound of the formula:

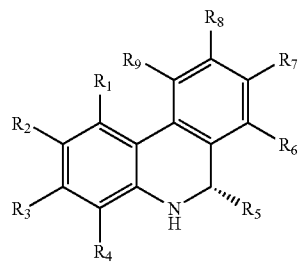

reacting said intermediate compound with an arylsulfonyl chloride of formula (V)

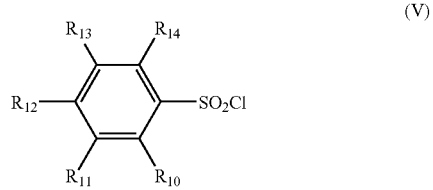

to produce the compound of formula (I).

26. The process of claim 25 wherein said intermediate compound is produced in the presence of an aprotic solvent.

27. The process of claim 26 wherein said aprotic solvent is dichloromethane.

28. The process of claim 25 wherein said reducing agent is a chiral sodium triacyloxyborohydride.

29. The process of claim 25 wherein $R_1$, $R_2$, $R_3$, $R_4$, $R_6$, $R_8$, $R_9$, $R_{10}$, $R_{11}$, $R_{13}$ and $R_{14}$ are each hydrogen.

30. The process of claim 29 where $R_5$ is methyl.

31. The process of claim 30 wherein $R_{12}$ is OH, $OCH_3$, sulfamate, or alkylcarbonate.

32. The process of claim 31 wherein $R_7$ is $C_1$-$C_{12}$ alkyl, $C_6$-$C_{20}$ aryl, or fluoro.

33. The process of claim 32 wherein $R_7$ is fluoro.

34. The process of claim 26 wherein $PG_1$ is phenol protecting group, further comprising removing the phenol protecting group thereby converting —O—$PG_1$ to OH.

35. A method of synthesizing a compound of formula (I):

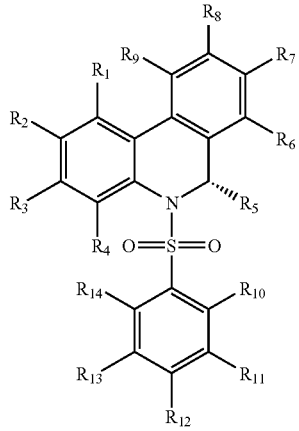

(I)

wherein:
R$_1$, R$_2$, R$_3$, R$_4$, R$_6$, R$_7$, R$_8$, R$_9$, R$_{10}$, R$_{13}$ and R$_{14}$ are, independently, hydrogen, C$_1$-C$_{12}$ alkyl, halogen, or C6-C10 aryl;

R$_5$ is C$_1$-C$_{12}$ alkyl or C6-C10 aryl; and

R$_{11}$ and R$_{12}$ are, independently, hydrogen or —O—PG$_1$ where PG$_1$ is hydrogen, a phenol protecting group, sulfamate, or alkylcarbonate;

comprising:
reacting a compound of formula (a1)

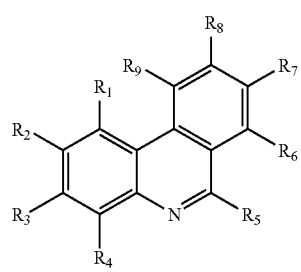

(a1)

with a chiral reducing agent, a metal borohydride and a halotrialkylsilane to produce an intermediate compound of the formula:

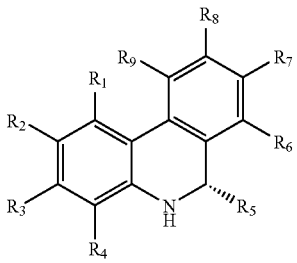

reacting said intermediate compound with an arylsulfonyl chloride of formula (V)

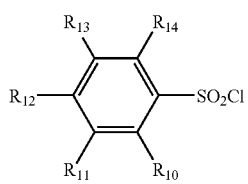

(V)

to produce the compound of formula (I).

36. The process of claim 35 wherein said intermediate compound is produced in the presence of an aprotic solvent.

37. The process of claim 36 wherein said aprotic solvent is dichloromethane.

38. The process of claim 35 wherein said chiral reducing agent is (R)-tetrahydro-1-methyl-3,3-diphenyl-1H,3H-pyrrolo[1,2-c][1,3,2]oxazaborole.

39. The process of claim 35 wherein the metal borohydide is sodium or lithium borohydride.

40. The process of claim 39 wherein step of reacting the compound of formula (a1) with a chiral reducing agent is performed in the presence of a halotrialkylsilane.

41. The process of claim 40 wherein the halotrialkylsilane is chlorotrimethylsilane.

42. The process of claim 35 wherein R$_1$, R$_2$, R$_3$, R$_4$, R$_6$, R$_8$, R$_9$, R$_{10}$, R$_{11}$, R$_{13}$ and R$_{14}$ are each hydrogen.

43. The process of claim 42 where R$_5$ is methyl.

44. The process of claim 43 wherein R$_{12}$ is OH, OCH$_3$, sulfamate, or alkylcarbonate.

45. The process of claim 44 wherein R$_7$ is C$_1$-C$_{12}$ alkyl, C6-C10 aryl, or fluoro.

46. The process of claim 45 wherein R$_7$ is fluoro.

47. The process of claim 35 wherein PG$_1$ is a phenol protecting group, further comprising removing the phenol protecting group thereby converting —O—PG$_1$ to OH.

48. The process of claim 10 wherein PG is [2-(trimethylsilyl)ethoxy]methyl and wherein said removing said amino protecting group comprises reacting the compound of formula (II) with tetrabutylammonium fluoride in THF.

* * * * *